US008846645B2

(12) United States Patent
Mayer et al.

(10) Patent No.: US 8,846,645 B2
(45) Date of Patent: Sep. 30, 2014

(54) CYCLOHEXANE COMPOUNDS AND THEIR USE AS ANTIBIOTICS

(75) Inventors: Günter Mayer, Bonn (DE); Christina Elsbeth Luense, Bonn (DE); Valentin Wittmann, Konstanz (DE); Magnus S. Schmidt, Konstanz (DE)

(73) Assignees: Rheinische Friedrich-Wilhelms Universität Bonn (DE); Universität Konstanz (DE)

( * ) Notice: Subject to any disclaimer, the term of this patent is extended or adjusted under 35 U.S.C. 154(b) by 0 days.

(21) Appl. No.: 13/990,801

(22) PCT Filed: Dec. 13, 2011

(86) PCT No.: PCT/EP2011/072597
§ 371 (c)(1),
(2), (4) Date: May 31, 2013

(87) PCT Pub. No.: WO2012/080240
PCT Pub. Date: Jun. 21, 2012

(65) Prior Publication Data
US 2014/0066409 A1    Mar. 6, 2014

(30) Foreign Application Priority Data
Dec. 14, 2010   (EP) .................... 10194929

(51) Int. Cl.
*A61K 31/66* (2006.01)
*A61K 31/13* (2006.01)
*C07C 211/25* (2006.01)
*C07F 9/44* (2006.01)
*C07F 9/53* (2006.01)
*C07C 215/42* (2006.01)
*C07C 233/23* (2006.01)
*C07F 9/117* (2006.01)
*C07C 215/44* (2006.01)

(52) U.S. Cl.
CPC .............. *C07F 9/44* (2013.01); *C07F 9/5304* (2013.01); *A61K 31/13* (2013.01); *A61K 31/66* (2013.01); *C07C 211/25* (2013.01); *C07C 215/42* (2013.01); *C07C 233/23* (2013.01); *C07C 2101/14* (2013.01); *C07F 9/117* (2013.01); *C07C 215/44* (2013.01)
USPC .............. 514/114; 514/579; 564/15; 564/462

(58) Field of Classification Search
CPC ...... A61K 31/66; A61K 31/13; C07F 9/5304; C07C 211/25
USPC ............................. 514/114, 579; 564/15, 462
See application file for complete search history.

(56) References Cited

U.S. PATENT DOCUMENTS 4,871,747 A   10/1989   Kinast

FOREIGN PATENT DOCUMENTS

WO    2006/100586 A1    9/2006

OTHER PUBLICATIONS

Seiichiro Ogawa et al. "Synthesis of DL-2-amino-2-deoxyvalidamine and its three diastereoisomers", Carbohydrate Research, 204 (1990) 51-64.
Seiichiro Ogawa et al. "New Synthesis of 2-Amino-Sa-carba-2-deoxy-<X-DL-glucopyranose and its Transformation into Valienamine and Valiolamine Analogues", Liebigs Ann. Chem. 1992,637-641.
Yasuhiro Kajihara et al. "Galactosyl transfer ability of B-( 1—+4)-galactosyltransferase toward 5a-carba-sugars", Carbohydrate Research 323 (2000) 44-48.
Gloria Rassu et al. Variable Strategy toward Carbasugars and Relatives. 6. Diastereoselective Synthesis of 2-Deoxy-2-amino-Sa-carba-beta-L-mannopyranuronic Acid and 2-Deoxy-2-amino-Sa-carba-beta-L-mannopyranose, J. Org. Chem. 2004, 69, 1625-1628.
Rezso Bognar et al. "2-Acetamido-2-deoxy-5-t:hio-D-glucopyranose (5-t:hio-N-acet:yi-D-glucosamine)", Carbohydrate Research, vol. 90, No. 1, Mar. 16, 1981 , pp. 138-143.
Tanahashi E et al: "A facile synthesis of 2-acetamido-2-deoxy-5-thio-d-glucopyranose", Carbohydrate Research, vol. 117, Jun. 16, 1983, pp. 304-308.
Greimel P et al: "Fluorescent glycosidase inhibiting 1,5-dideoxy-1,5-iminoalditols", Bioorganic & Medicinal Chemistry Letters, vol. 16, No. 8, Apr. 15, 2006 , pp. 2067-2070.
Al-Rawi, Samy et al: "Synthesis and Biochemical Properties of Reversible Inhibitors of UDP-N-Acetylglucosamine 2-Epimerase", Angewandte Chemie International Edition, vol. 43, 2004, pp. 4366-4370.
Ching-Wen Ho et al: "Development of GlcNAc-Inspired Iminocyclitiols as Potent and Selective N-Acetyl-beta-Hexosaminidase Inhibitors", ACS Chemical Biology, vol. 5, No. 5, Feb. 27, 2010, pp. 489-497.
Steiner A J et al: "2-Acetamino-1,2-dideoxynojirimycin-lysine hybrids as hexosaminidase inhibitors", Tetrahedron Asymmetry, vol. 20, No. 6-8, May 7, 2009, pp. 832-835.
Le Merrer, Yves et al: "Synthesis of Azasugars as Potent Inhibitors of Glycosidases", Bioorganic & Medicinal Chemistry, vol. 5, No. 3, 1997, pp. 519-533.
Miyamoto, M. et al. "Synthesis of the Carbon Pseudosugar Analog of Lipid X", Tetrahedron Lett. vol. 33, 1992, pp. 3725-3728.
Barton et al., Synthetic Methods for the Preparation of Basic D- and L Pseudo-Sugars. Synthesis of Carbocyclic Analogues of N-Acetyl-Muramyl-L-Alanyl-D-Isoglutamine (MDP), Tetrahedron vol. 46, 1990, pp. 215-230.
International Search Report; PCT/EP2011/072597; Int' File Date: Dec. 13, 2011; Rheinische Friedrich-Wilhelms Universitaet; 6 pgs.

Primary Examiner — Raymond Henley, III
(74) Attorney, Agent, or Firm — Schmeiser, Olsen & Watts, LLP

(57) ABSTRACT

The present invention relates to compounds according to general formula (I), pharmaceutical compositions comprising compounds according to general formula (I) and the use of the compounds for the treatment of a bacterial infection, particularly for use as an antibiotic.

17 Claims, 6 Drawing Sheets

SEQUENCE LISTING

```
<160> NUMBER OF SEQ ID NOS: 2

<210> SEQ ID NO 1
<211> LENGTH: 45
<212> TYPE: DNA
<213> ORGANISM: Artificial Sequence
<220> FEATURE:
<223> OTHER INFORMATION: 5-Primer

<400> SEQUENCE: 1
gataatacga ctcactatag ggcagttaaa gcgcctgtgc aaata           45

<210> SEQ ID NO 2
<211> LENGTH: 30
<212> TYPE: DNA
<213> ORGANISM: Artificial Sequence
<220> FEATURE:
<223> OTHER INFORMATION: 3-Primer

<400> SEQUENCE: 2
atcttattaa ctttgtccat taagtcaccc           30
```

CYCLOHEXANE COMPOUNDS AND THEIR USE AS ANTIBIOTICS

FIELD OF TECHNOLOGY

The present invention relates to cyclohexane compounds according to general formula (I) and pharmaceutical compositions comprising compounds according to general formula (1). In particular, the present invention relates to the use of the compounds for the treatment of a bacterial infection, particularly for use as an antibiotic.

BACKGROUND

Since the discovery of antibiotic substances and their use against microbes, bacteria have evolved to defend themselves by acquiring resistances. Especially in hospitals where bacteria are exposed to a wide array of antibacterial substances, strains arose that are multiresistant. A prominent example for this is the multiresistant Staphylococcus aureus (MRSA) against which vancomycin used to be a reliable cure, until the strains Vancomycin-Intermediate/Resistant Staphylococcus aureus (VISA/VRSA) started to appear, which are also resistant against this last defence.

The mechanisms of resistance are usually tightly intertwined with the mode of action of the antibiotic. Therefore, the resistance against one representative of a certain antibiotics class yields to resistance against the entire group with the same mode of action. This is why it is not only necessary to have an ongoing search for new antibiotic substances, but to also find and use new antibacterial targets enforcing new mechanisms of action.

In the past the mode of action for several antibacterial compounds was revealed to be inter alia the targeting of riboswitches. To date metabolite analogues have been described which modulate thiamine pyrophosphate (TPP), lysine, flavin mononucleotide (FMN) or purine riboswitches.

Riboswitches have appeared as one of these new promising targets for antibacterial defence. Riboswitches, which regulate 2-4% of all bacterial genes, are found in the 5'-untranslated region (5' UTR) of bacterial mRNA and consist of an aptamer and an expression domain. Upon metabolite binding, a change in secondary structure leads to termination of transcription or inhibition of translation initiation. Amongst them the glmS riboswitch (glucosamine-6-phosphate synthetase riboswitch) which is predicted to exist in at least 18 Gram-positive organisms has an exceptional mechanism of regulation. The glmS riboswitch binds glucosamine-6-phosphate to regulate glucosamine-6-phosphate synthetase (glmS) genes. Once glucosamine-6-phosphate binds, this riboswitch acts as a ribozyme, resulting in cleavage of the 5' end of the riboswitch.

Antibiotic resistance creates a permanent need for new antibacterial targets. Thus, it would be desirable to provide compounds that target the glmS riboswitch and exhibit antimicrobial activity.

Therefore, the object underlying the present invention was to provide compounds that are usable as antibiotic.

BRIEF SUMMARY

The problem is solved by a compound according to general formula (I) as given as follows and/or racemates, enantiomers, diastereomers, solvates, hydrates, and pharmaceutically acceptable salts and/ or esters thereof:

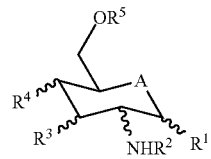

wherein:
- $R^1$ is selected from the group comprising H, OH, SH and/or $NH_2$;
- $R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;
- $R^3$ is selected from the group comprising OH, SH and/or $NH_2$;
- $R^4$ is selected from the group comprising OH, SH and/or $NH_2$;
- $R^5$ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

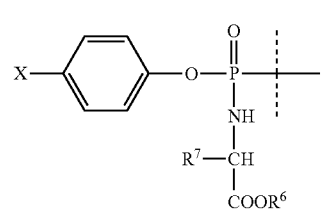

wherein:
- $R^6$ is selected from the group comprising linear or branched $C_1$-$C_6$-alkyl, benzyl and/or cyclohexyl;
- $R^7$ is a side chain of an amino acid selected from the group comprising hydrogen; linear or branched $C_1$-$C_4$-alkyl; linear or branched alkyl groups of the type —$C_nH_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$—$C_6H_4$—Y wherein Y is selected from the group comprising OH, SH, $C_1$-$C_3$-alkyl and/or $NH_2$; —$CH_2$-imidazole; —$CH_2$-indole; —$CH_2$-(furanyl-3-yl); —$CH_2$-(pyridyl-3-yl) and/or —$CH_2$— (imidazolyl-3-yl);
- X is selected from the group comprising Cl, Br, I, $C_1$-$C_6$-alkyl and/or $C_1$-$C_6$-alkoxy;
- A is selected from the group comprising S, $NR^8$, $C=CR^8R^9$ and/or $CR^8R^9$, wherein
  - $R^8$, $R^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker.

Furthermore, the invention relates to a pharmaceutical composition comprising a compound according to the invention as an active ingredient, the use of a compound according to the invention in the treatment of a bacterial infection and a method for preparing such compounds. Preferred embodiments of compounds are given in the dependant claims.

Surprisingly it was found that a compound according to the invention can exhibit an affinity to the glmS riboswitch (glucosamine-6-phosphate synthetase riboswitch) and is able to activate the glmS riboswitch. Beneficially, the compounds according to the invention can be useful as an antibacterial substance in the treatment of bacterial infection. The present invention therefore provides a novel approach to the treatment of bacterial infection.

DETAILED DESCRIPTION OF THE DISCLOSURE

Figure 1:
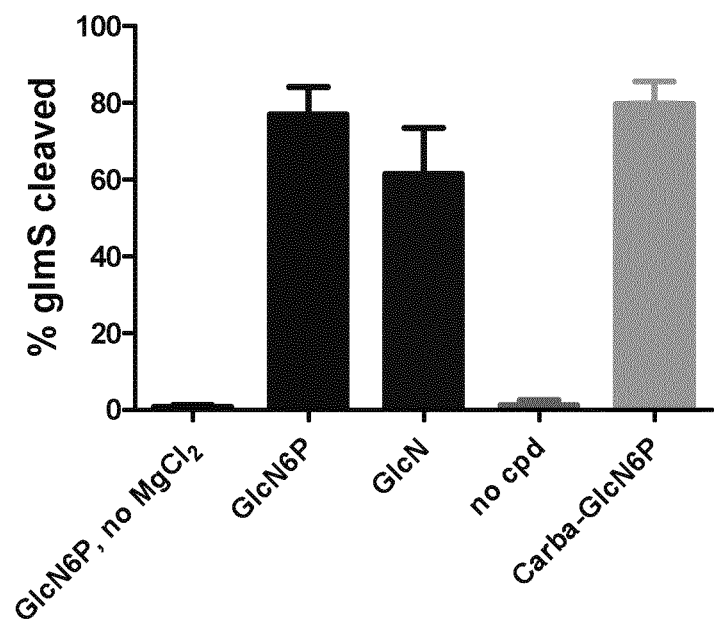
FIG. 1 in vitro activation of the self cleavage of the glmS riboswitch by the natural metabolite glucosamine-6-phosphate (GlcN6P), glucosamine (GlcN) and by the compound according to formula (1), Carba-glucosamine-6-phosphate (Carba-GlcN6P)

The term "alkyl" according to the invention is to be understood as meaning straight-chain or branched alkyl groups. The term "C1-C10-alkyl" as used herein refers to straight-chain or branched alkyl groups having 1 to 10 carbon atoms. Preferred C1-C10-alkyl groups are selected from the group comprising methyl, ethyl and the isomers of propyl, butyl, pentyl, hexyl, heptyl or octyl, such as, for example, isopropyl, isobutyl, tert.-butyl, sec.-butyl and/or isopentyl. Especially preferred are C1-C5-alkyl groups selected from the group comprising methyl, ethyl and/or isopropyl.

The term "alkenyl" according to the invention is to be understood as meaning straight-chain or branched alkyl groups having at least one or several double bonds. The term "$C_2$-$C_{10}$-alkenyl" as used herein refers to straight-chain or branched alkenyl groups having 2 to 10 carbon atoms and at least one or several double bonds. Preferred $C_2$-$C_{10}$-alkenyl groups are selected from the group comprising ethylen-1-yl, propen-1-yl, allyl, buten-1-yl, buten-2-yl and/or buten-3-yl.

The term "$C_6$-$C_{10}$-aryl" according to the invention is to be understood as meaning aromatic groups having 6 to 10 carbon atoms. Preferably, the term "$C_6$-$C_{10}$-aryl" refers to carbocycles. Preferred $C_6$-$C_{10}$-aryl is selected from the group comprising phenyl or naphthyl.

The term "arylalkyl" according to the invention unless specifically stated otherwise is to be understood as meaning a group which bonds by the respective last-mentioned group, referring to "arylalkyl" by the alkyl group.

The term "$C_7$-$C_{14}$-arylalkyl wherein the aryl group has 6 to 10 carbon atoms and the alkyl group has 1 to 4 carbon atoms" preferably is a group phenylalkyl wherein the alkyl has 1 to 4 carbon atoms, more preferably selected from the group comprising benzyl, phenylethyl and/or phenylbutyl.

The term "alkyloxy" according to the invention is to be understood as meaning an alkyl group connected to the oxy connecting atom unless specifically stated otherwise. The term "$C_1$-$C_6$-alkyloxy" as used herein refers to an alkyloxy group having 1 to 6 carbon atoms. $C_1$-$C_6$-alkyloxy groups are preferably selected from the group comprising methoxy, ethoxy, n-propoxy, isopropoxy and/or butoxy.

The term "amino acid" according to the invention is to be understood as meaning alpha amino acids, molecules containing both amine and carboxyl functional groups attached to the same carbon, which is called the alpha-carbon. The term "amino acid" according to the invention is to be understood as being broadly defined to include any modified and unusual amino acid. Preferred amino acids are naturally occurring amino acids. Representative amino acids include, but are not limited to, the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline. The various alpha amino acids differ in which side chain is attached to their alpha carbon.

The term "side chains of amino acids" according to the invention is to be understood as meaning the groups attached to the alpha carbon of alpha-amino acids. For example the side chains of glycine, alanine, valine, leucine and phenylalanine are hydrogen, methyl, iso-propyl, isobutyl and benzyl, respectively.

Preferably, the substituent A is selected from the group comprising S, $NR^8$ and/or $CR^8R^9$, wherein $R^8$ and $R^9$ are selected, the same or each independently of the other, from the group comprising hydrogen, $C_1$-$C_5$-alkyl, $C_6$-$C_{10}$-aryl, or $C_2$-$C_5$-alkenyl.

In a preferred embodiment, the element A is a group —$CH_2$— and the compound has the formula (III) as indicated below and/or racemates, enantiomers, diastereomers, solvates, hydrates, and pharmaceutically acceptable salts and/or esters thereof:

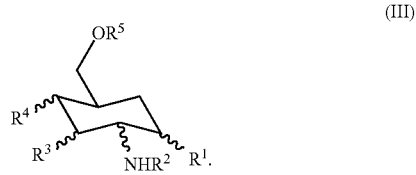

(III)

Advantageously, the compound according to the formula (III) can exhibit a good affinity to the glmS riboswitch and can be particularly useful as an antibacterial substance in the treatment of bacterial infection.

Preferably, the substituent $R^1$ is a hydroxyl group. Further, the substituent $R^1$ can be hydrogen. Further preferred, the substituent $R^3$ is a hydroxyl group. Further preferred, the substituent $R^4$ is a hydroxyl group. In a preferred embodiment of the compound according to the invention the substituents R', and $R^4$ are OH. In another preferred embodiment of the compound according to the invention the substituent $R^1$ is hydrogen and the substituents $R^3$ and $R^4$ are OH.

Advantageously, the substituents $R^1$, $R^3$ and $R^4$ being a hydroxyl group can result in a substantial increase in activation of the glmS riboswitch by the compounds according to the invention.

In a preferred embodiment, the substituent $R^2$ is selected from the group comprising hydrogen, $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Most preferred, the substituent $R^2$ is hydrogen. Further preferred, the substituent $R^2$ is selected from the group comprising $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Preferred are small alkyl, acyl and ester groups selected from methyl, ethyl, $C(O)CH_3$, $C(O)C_2H_5$, $OC(O)CH_3$, $OC(O)C_2H_5$, and benzyl. It is also preferred that the substituent $R^2$ is selected from $C(O)NH_2$, $NH_2$ or $S(O)_2OH$. These substituents can show a good activity and activation of the glmS riboswitch.

Preferably, the substituent $R^5$ is selected from the group comprising hydrogen, $P(O)(OH)_2$ and/or aryloxy phosphoramidates according to formula (II) wherein $R^6$ is methyl, ethyl, isopropyl, cyclohexyl or benzyl, X is methoxy and $R^7$ is methyl or another side chain of an amino acid. Preferably, the substituent $R^5$ is hydrogen. Most preferred, the substituent $R^5$ is $P(O)(OH)_2$. Advantageously, in vitro screenings monitoring the ribozyme-catalyzed cleavage reaction showed that compounds wherein the substituent $R^5$ is hydrogen or $P(O)(OH)_2$ are capable of efficiently activating the glmS riboswitch.

Further preferred, the substituent $R^5$ is an aryloxy phosphoramidate according to formula (II). Preferred are aryloxy phosphoramidates wherein $R^6$ is methyl, ethyl, isopropyl, cyclohexyl or benzyl, X is methoxy and $R^7$ is methyl or another side chain of an amino acid. The therapeutic potential of antibacterial compounds can be effectively improved by prodrug technologies aimed at delivering the monophosphates into cells. Via prodrug technologies a prodrug is delivered into the cell, where it may then be further converted to the active species. By an aryloxy phosphoramidate the charges of the phosphate group are fully masked which can provide an efficient passive cell-membrane penetration. Upon entering the cell, the masking groups are enzymatically cleaved to release the phosphorylated molecule.

Aryloxy phosphoramidates according to formula (II) wherein $R^6$ is selected from the group comprising linear or branched $C_1$-$C_6$-alkyl, benzyl and/or cyclohexyl, and $R^7$ is a side chain of an amino acid, and X is selected from the group comprising Cl, Br, I, $C_1$-$C_6$-alkyl and/or $C_1$-$C_6$-alkoxy are designed to deliver a monophosphate inside cells. Inside the cell, the monophosphate can be restored. Without being bound to a special theory, it is assumed that after enzymatic, for example by an esterase-mediated, cleavage of $R^6$ an intermediate metabolite can be spontaneously converted into an amino acyl metabolite by liberating the phenyl ring through intramolecular nucleophilic reaction leaving only the remaining amino acid to be released from the phosphate group.

The substituent $R^7$ is a side chain of an amino acid. Preferably, the substituent $R^7$ is a side chain of a naturally occurring amino acid selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline, preferably alanine, phenylalanine, proline, valine, leucine, isoleucine, glycine, methionine, and α,α-dimethylglycine.

In preferred embodiments the substituent $R^7$ is a linear or branched alkyl group of the type —$C_nH_{2n}$-U-D wherein n is 1, 2, 3 or 4, U is selected from the group comprising O, CO, COO, CONH, S, guanidine and/or NH, and D is selected from the group comprising H and/or methyl; —$CH_2$—$C_6H_4$—OH; —$CH_2$-imidazole and/or —$CH_2$-indole. Preferably, the substituent $R^7$ is a side chain of an amino acid selected from the group comprising linear or branched $C_1$-$C_4$-alkyl.

In a preferred embodiment, the substituent $R^5$ is selected from the group comprising hydrogen, $P(O)(OH)_2$ and/or aryloxy phosphoramidates according to formula (II) wherein $R^6$ is methyl, ethyl, isopropyl, cyclohexyl or benzyl, X is methoxy and $R^7$ is methyl.

In especially preferred embodiments, the compound is selected from the group comprising the formulas (1) and/or (2) as indicated below and/or racemates, enantiomers, diastereomers, solvates, hydrates, and pharmaceutically acceptable salts and/or esters thereof:

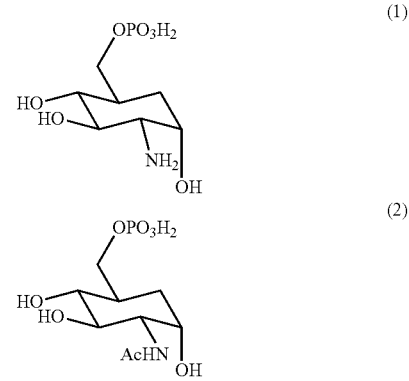

wherein
Ac is acetyl.

Advantageously, in vitro screenings monitoring the ribozyme-catalyzed cleavage reaction showed that particularly the compounds according to formula (1) was capable of efficiently activating the glmS riboswitch. Particularly, the compound according to formula (1) was able to activate the riboswitch in comparable levels to the natural metabolite glucosamine-6-phosphate (GlcN6P). Advantageously, the compounds represent promising candidates for the development of antibacterial compounds.

The compounds described herein contain one or more asymmetric centres and may thus give rise to stereo isomers (configurational isomers). The present invention includes all such possible stereo isomers as well as their mixtures, and pharmaceutically acceptable salts thereof.

Unless specifically stated otherwise, compounds, groups or substituents denoted with Arabic numerals and such compounds, groups or substituents denoted with Roman numerals differ from each other, that is, compounds, groups or substituents are different compounds, groups or substituents.

Further preferred, the compound according to general formula (I) can be part of a dimer, trimer or oligomer, formed from one compound according to the invention and at least one other compound joined together via a linker linked to element A. Preferably the linker is selected from the group comprising nucleotide linkers, polyethylene glycols, peptide linkers and/or linear or branched, saturated or unsaturated $C_1$-$C_{50}$-alkyl.

Preferably, a nucleotide linker has a length in the range of ≥1 nucleotide to ≤30 nucleotides, preferred in the range of ≥2 nucleotides to ≤15 nucleotides, further preferred in the range of ≥5 nucleotides to ≤15 nucleotides, more preferred in the range of ≥10 nucleotides to ≤15 nucleotides, wherein the nucleotides are selected from the group comprising guanosine, cytidine, adenosine and/or thymidine. A preferred nucleotide is adenosine. Especially preferred linkers are Poly A-linkers. Preferably, a polyethylene glycol linker comprises 1 to 15 polyethylene glycol units, preferred in the range of 1 to 10 polyethylene glycol units, more preferred in the range of 2 to 8 polyethylene glycol units. Preferred are linear polyethylene glycol (PEG) units HO—$(CH_2CH_2O)_n$—H, wherein n is an integer in the range of 1 to 15, preferred in the range of 1 to 10, more preferred in the range of 2 to 8. In preferred embodiments the linker is a peptide linker, wherein the peptide linker preferably comprises amino acids selected from the group comprising glycine, alanine and/or β-alanine. Preferably, the peptide linker comprises in the range of 2 to 4 amino acids. Preferably, the peptide linker comprises β-β-alanine units. Preferably, the peptide linker comprises in the range of 2 to 4 β-alanine units. In preferred embodiments the linker is a linear or branched, saturated or unsaturated $C_1$-$C_{40}$-alkyl group, preferred a $C_1$-$C_{30}$ alkyl group, more preferred a $C_2$-$C_{20}$— alkyl group Preferably, the linker is an alkyl group —$(CH_2)_n$— wherein n is an integer in the range of 1 to 40, preferred in the range of 1 to 30, further preferred in the range of 2 to 20, more preferred in the range of 2 to 18, even more preferred n is 2, 6, 12 or 18.

A further aspect of the present invention relates to a compound according to general formula (I) as given as follows and/or racemates, enantiomers, diastereomers, solvates, hydrates, and pharmaceutically acceptable salts and/or esters thereof:

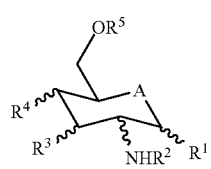

(I)

wherein:
$R^1$ is selected from the group comprising H, OH, SH and/or $NH_2$;
$R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;
$R^3$ is selected from the group comprising OH, SH and/or $NH_2$;
$R^4$ is selected from the group comprising OH, SH and/or $NH_2$;

$R^5$ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

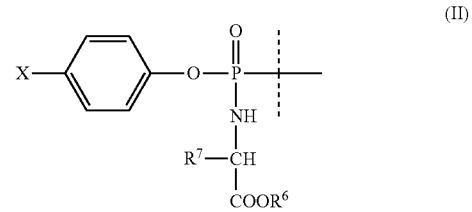

(II)

wherein:
$R^6$ is selected from the group comprising linear or branched $C_1$-$C_6$-alkyl, benzyl and/or cyclohexyl;
$R^7$ is a side chain of an amino acid selected from the group comprising hydrogen; linear or branched $C_1$-$C_4$-alkyl; linear or branched alkyl groups of the type —$C_nH_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$—$C_6H_4$—Y wherein Y is selected from the group comprising OH, SH, $C_1$-$C_3$-alkyl and/or $NH_2$; —$CH_2$-imidazole; —$CH_2$-indole; —$CH_2$-furanyl-3-yl); —$CH_2$-(pyridyl-3-yl) and/or —$CH_2$— (imidazolyl-3-yl);
X is selected from the group comprising Cl, Br, I, $C_1$-$C_6$-alkyl and/or $C_1$-$C_6$-alkoxy;
A is selected from the group comprising S, $NR^8$, C=$CR^8R^9$ and/or $CR^8R^9$, wherein
$R^8$, $R^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker,
for use as a medicament.

Preferably, the substituent A is selected from the group comprising S, $NR^8$ and/or $CR^8R^9$, wherein $R^8$ and $R^9$ are selected, the same or each independently of the other, from the group comprising hydrogen, $C_1$-$C_5$-alkyl, $C_6$-$C_{10}$-aryl, or $C_2$-$C_5$-alkenyl. In a preferred embodiment, the element A is a group —$CH_2$— and the compound has the formula (III) as indicated below and/or racemates, enantiomers, diastereomers, solvates, hydrates, and pharmaceutically acceptable salts and/or esters thereof:

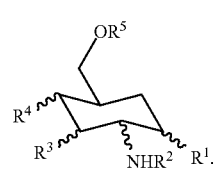

(III)

Preferably, the substituent $R^1$ is a hydroxyl group. Further, the substituent $R^1$ can be hydrogen. Further preferred, the substituent $R^3$ is a hydroxyl group. Further preferred, substituent $R^4$ is a hydroxyl group. In a preferred embodiment of the compound according to the invention the substituents $R^1$, $R^3$ and $R^4$ are OH. In another preferred embodiment of the compound according to the invention the substituent $R^1$ is hydrogen and the substituents $R^3$ and $R^4$ are OH.

In a preferred embodiment, the substituent $R^2$ is selected from the group comprising hydrogen, $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Most preferred, the substituent $R^2$ is hydrogen. Further preferred, the substituent $R^2$ is selected from the group comprising $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Preferred are small alkyl, acyl and ester groups selected from methyl, ethyl, $C(O)CH_3$, $C(O)C_2H_5$, $OC(O)CH_3$, $OC(O)C_2H_5$, and benzyl. It is also preferred that the substituent $R^2$ is selected from $C(O)NH_2$, $NH_2$ or $S(O)_2OH$.

Preferably, the substituent $R^5$ is selected from the group comprising hydrogen, $P(O)(OH)_2$ and/or aryloxy phosphoramidates according to formula (II) wherein $R^6$ is selected from the group comprising methyl, ethyl, isopropyl, cyclohexyl and benzyl, X is methoxy and $R^7$ is methyl or another side chain of an amino acid. Preferably, the substituent $R^5$ is hydrogen. Most preferred, the substituent $R^5$ is $P(O)(OH)_2$. Further preferred, the substituent $R^5$ is an aryloxy phosphoramidate according to formula (II). Preferred are aryloxy phosphoramidates wherein $R^6$ is methyl, ethyl, isopropyl, cyclohexyl or benzyl, X is methoxy and $R^7$ is methyl or another side chain of an amino acid.

The substituent $R^7$ is a side chain of an amino acid. Preferably, the substituent $R^7$ is a side chain of a naturally occurring amino acid selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline, preferably alanine, phenylalanine, proline, valine, leucine, isoleucine, glycine, methionine, or α,α-dimethylglycine. In preferred embodiments, the substituent $R^7$ is a linear or branched alkyl groups of the type —$C_nH_{2n}$-U-D wherein n is 1, 2, 3 or 4, U is selected from the group comprising O, CO, COO, CONH, S, guanidine and/or NH, and D is selected from the group comprising H and/or methyl; —$CH_2$—$C_6H_4$—OH; —$CH_2$-imidazole and/or —$CH_2$-indole. Preferably, the substituent $R^7$ is a side chain of an amino acid selected from the group comprising hydrogen; linear or branched $C_1$-$C_4$-alkyl, most preferred methyl.

In a preferred embodiment, the substituent $R^5$ is selected from the group comprising hydrogen, $P(O)(OH)_2$ and/or aryloxy phosphoramidates according to formula (II) wherein $R^6$ is methyl, ethyl, isopropyl, cyclohexyl or benzyl, X is methoxy and $R^7$ is methyl.

In especially preferred embodiments, the compound is selected from the group comprising the formulas (1), (2), (3) and/or (4) as indicated below and/or racemates, enantiomers, diastereomers, solvates, hydrates, and pharmaceutically acceptable salts and/or esters thereof:

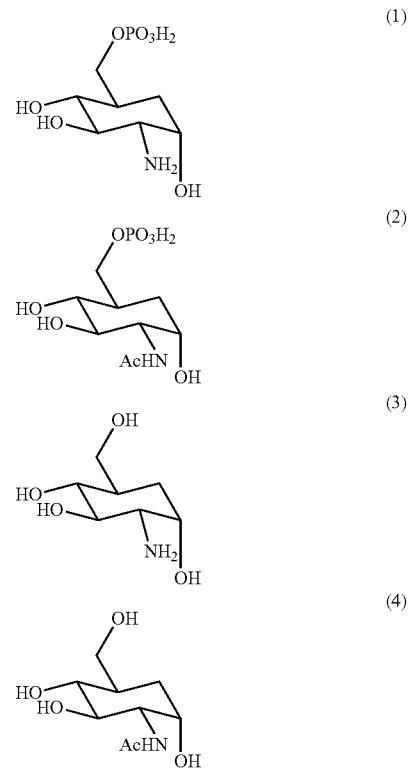

wherein
Ac is acetyl.

In an especially preferred embodiment, the compound is selected from the group comprising the formulas (1) and/or (2) as indicated above and/or racemates, enantiomers, diastereomers, solvates, hydrates, and pharmaceutically acceptable salts and/or esters thereof.

Further preferred, the compound according to general formula (I) can be part of a dimer, trimer or oligomer, formed from one compound according to the invention and at least one other compound joined together via a linker linked to element A. Preferably the linker is selected from the group comprising nucleotide linkers, polyethylene glycols, peptide linkers and/or linear or branched, saturated or unsaturated $C_1$-$C_{50}$-alkyl.

Preferably, a nucleotide linker has a length in the range of ≥1 nucleotide to ≤30 nucleotides, preferred in the range of ≥2 nucleotides to ≤15 nucleotides, further preferred in the range of ≥5 nucleotides to ≤15 nucleotides, more preferred in the range of ≥10 nucleotides to ≤15 nucleotides, wherein the nucleotides are selected from the group comprising guanosine, cytidine, adenosine and/or thymidine. A preferred nucleotide is adenosine. Especially preferred linkers are Poly A-linkers. Preferably, a polyethylene glycol linker comprises 1 to 15 polyethylene glycol units, preferred in the range of 1 to 10 polyethylene glycol units, more preferred in the range of 2 to 8 polyethylene glycol units. Preferred are linear polyethylene glycol (PEG) units HO—$(CH_2CH_2O)_n$—H, wherein n is an integer in the range of 1 to 15, preferred in the range of 1 to 10, more preferred in the range of 2 to 8. In preferred embodiments the linker is a peptide linker, wherein the peptide linker preferably comprises amino acids selected from the group comprising glycine, alanine and/or β-alanine. Preferably, the peptide linker comprises in the range of 2 to 4 amino acids. Preferably, the peptide linker comprises β-β- alanine units. Preferably, the peptide linker comprises in the range of 2 to 4 β-alanine units. In preferred embodiments the linker is a linear or branched, saturated or unsaturated $C_1$-$C_{40}$-alkyl group, preferred a $C_1$-$C_{30}$ alkyl group, more preferred a $C_2$-$C_{20}$-alkyl group Preferably, the linker is an alkyl group —$(CH_2)_n$— wherein n is an integer in the range of 1 to 40, preferred in the range of 1 to 30, further preferred in the range of 2 to 20, more preferred in the range of 2 to 18, even more preferred n is 2, 6, 12 or 18.

A further aspect of the present invention relates to a compound according to general formula (I) as given as follows and/or racemates, enantiomers, diastereomers, solvates, hydrates, and pharmaceutically acceptable salts and/or esters thereof:

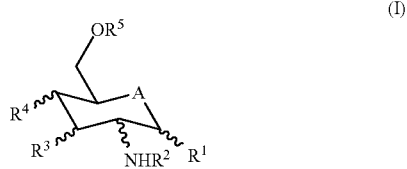

(I)

wherein:
R$^1$ is selected from the group comprising H, OH, SH and/or NH$_2$;
R$^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, C(O)$C_1$-$C_{10}$-alkyl, OC(O)$C_1$-$C_{10}$-alkyl, C(O)O$C_1$-$C_{10}$-alkyl, C(O)NH$_2$, NH$_2$ and/or S(O)$_2$OH;
R$^3$ is selected from the group comprising OH, SH and/or NH$_2$;
R$^4$ is selected from the group comprising OH, SH and/or NH$_2$;
R$^5$ is selected from the group comprising hydrogen, P(O)(OH)$_2$, S(O)$_2$OH, P(S)(OH)$_2$, P(O)OHSH, S(O)$_2$SH and/or aryloxy phosphoramidates according to general formula (II)

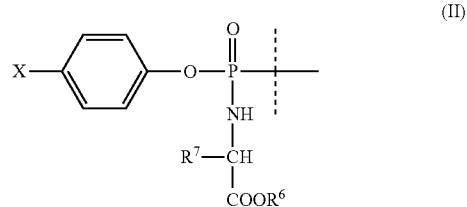

(II)

wherein:
R$^6$ is selected from the group comprising linear or branched $C_1$-$C_6$-alkyl, benzyl and/or cyclohexyl;
R$^7$ is a side chain of an amino acid selected from the group comprising hydrogen; linear or branched $C_1$-$C_4$-alkyl; linear or branched alkyl groups of the type —$C_nH_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —CH$_2$—$C_6H_4$—Y wherein Y is selected from the group comprising OH, SH, $C_1$-$C_3$-alkyl and/or NH$_2$; —CH$_2$-imidazole; —CH$_2$-indole; —CH$_2$—(furanyl-3-yl); —CH$_2$-(pyridyl-3-yl) and/or —CH$_2$—(imidazolyl-3-yl);

X is selected from the group comprising Cl, Br, I, $C_1$-$C_6$-alkyl and/or $C_1$-$C_6$-alkoxy;
A is selected from the group comprising S, NR$^B$, C=CR$^8$R$^9$ and/or CR$^8$R$^9$, wherein
R$^8$, R$^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, C(O)$C_1$-$C_{10}$-alkyl, C(O)O$C_1$-$C_{10}$-alkyl, C(O)NH$_2$, NH$_2$, S(O)$_2$OH and/or a linker, for use in the therapeutic and/or prophylactic treatment of a bacterial infection, particularly for use as an antibiotic.

The term "prophylactic treatment" according to the invention is to be understood as meaning that the compositions according to the invention can be applied before symptoms of the bacterial infection are manifest. Especially, the term "prophylactic treatment" is to be understood as meaning a medical treatment. It can be preferred to use the compounds according to the invention in a prophylactic treatment.

Surprisingly it was found that the compounds according to the general formula (I) can be effective against bacterial growth. Especially, the compounds according to formulas (1) and (3) were found to effectively inhibit the growth of *Staphylococcus aureus*.

One particular advantage of the compounds according to the invention is that the compounds are especially usable as an antibiotic, particularly against the multiresistant *Staphylococcus aureus* strain.

Preferably, the substituent A is selected from the group comprising S, NR$^8$ and/or CR$^8$R$^9$, wherein R$^8$ and R$^9$ are selected, the same or each independently of the other, from the group comprising hydrogen, $C_1$-$C_5$-alkyl, $C_6$-$C_{10}$-aryl, or $C_2$-$C_5$-alkenyl. In a preferred embodiment, the element A is a group —CH$_2$— and the compound has the formula (III) as indicated below and/or racemates, enantiomers, diastereomers, solvates, hydrates, and pharmaceutically acceptable salts and/or esters thereof:

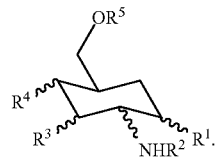

(III)

Preferably, the substituent R$^1$ is a hydroxyl group. Further, the substituent R$^1$ can be hydrogen. Further preferred, the substituent R$^3$ is a hydroxyl group. Further preferred, the substituent R$^4$ is a hydroxyl group. In a preferred embodiment of the compound according to the invention the substituents R', and R$^4$ are OH. In another preferred embodiment of the compound according to the invention the substituent R$^1$ is hydrogen and the substituents R$^3$ and R$^4$ are OH.

In a preferred embodiment, the substituent R$^2$ is selected from the group comprising hydrogen, $C_1$-$C_5$-alkyl preferably methyl, ethyl or n-propyl, benzyl, $C_1$-$C_5$-acyl preferably C(O)CH$_3$, C(O)$C_2H_5$, C(O)n-propyl or C(O)iso-propyl, $C_1$-$C_5$-alkylester preferably OC(O)CH$_3$, OC(O)$C_2H_5$, OC(O)n-propyl or OC(O)iso-propyl, C(O)NH$_2$, NH$_2$ and/or S(O)$_2$OH. Most preferred, the substituent R$^2$ is hydrogen. Further preferred, the substituent R$^2$ is selected from the group comprising $C_1$-$C_5$-alkyl preferably methyl, ethyl or n-propyl, benzyl, $C_1$-$C_5$-acyl preferably C(O)CH$_3$, C(O)

C₂H₅, C(O)n-propyl or C(O)iso-propyl, $C_1$-$C_5$-alkylester preferably OC(O)CH₃, OC(O)C₂H₅, OC(O)n-propyl or OC(O)iso-propyl, C(O)NH₂, NH₂ and/or S(O)₂OH. Preferred are small alkyl, acyl and ester groups selected from methyl, ethyl, C(O)CH₃, C(O)C₂H₅, OC(O)CH₃, OC(O)C₂H₅, and benzyl. It is also preferred that the substituent $R^2$ is selected from C(O)NH₂, NH₂ or S(O)₂OH.

Preferably, the substituent $R^5$ is selected from the group comprising hydrogen, P(O)(OH)₂ and/or aryloxy phosphoramidates according to formula (II) wherein $R^6$ is selected from the group comprising methyl, ethyl, isopropyl, cyclohexyl and benzyl, X is methoxy and $R^7$ is methyl or another side chain of an amino acid. Preferably, the substituent $R^5$ is hydrogen. Most preferred, the substituent $R^5$ is P(O)(OH)₂. Further preferred, the substituent $R^5$ is an aryloxy phosphoramidate according to formula (II). Preferred are aryloxy phosphoramidates wherein $R^6$ is methyl, ethyl, isopropyl, cyclohexyl or benzyl, X is methoxy and $R^7$ is methyl or another side chain of an amino acid.

The substituent $R^7$ is a side chain of an amino acid. Preferably, the substituent $R^7$ is a side chain of a naturally occurring amino acid selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline, preferably alanine, phenylalanine, proline, valine, leucine, isoleucine, glycine, methionine, or α,α-dimethylglycine. In preferred embodiments, the substituent $R^7$ is a linear or branched alkyl groups of the type —$C_nH_{2n}$-U-D wherein n is 1, 2, 3 or 4, U is selected from the group comprising O, CO, COO, CONH, S, guanidine and/or NH, and D is selected from the group comprising H and/or methyl; —CH₂—C₆H₄—OH; —CH₂-imidazole and/or —CH₂-indole. Preferably, the substituent $R^7$ is a side chain of an amino acid selected from the group comprising hydrogen; linear or branched $C_1$-$C_4$-alkyl, most preferred methyl.

In a preferred embodiment, the substituent $R^5$ is selected from the group comprising hydrogen, P(O)(OH)₂ and/or aryloxy phosphoramidates according to formula (II) wherein $R^6$ is methyl, ethyl, isopropyl, cyclohexyl or benzyl, X is methoxy and $R^7$ is methyl.

In a preferred embodiment, the compound according to general formula (I) for use in the therapeutic and/or prophylactic treatment of a bacterial infection, particularly for use as an antibiotic, comprises an element A being a group —CH₂—, the substituents $R^1$, $R^3$, and $R^4$ being OH, $R^2$ is hydrogen or C(O)CH₃, and $R^5$ is hydrogen or P(O)(OH)₂.

In especially preferred embodiments, the compound is selected from the group comprising the formulas (1), (2), (3) and/or (4) as indicated above and/or racemates, enantiomers, diastereomers, solvates, hydrates, and pharmaceutically acceptable salts and/or esters thereof. The compounds according to the general formulas (1), (2), (3) and (4) can be effective in the treatment of a bacterial infection, particularly as an antibiotic. Especially, the compounds according to formulas (1) and (3) were found to effectively inhibit bacterial growth of *Staphylococcus aureus*.

Further preferred, the compound according to general formula (I) can be part of a dimer, trimer or oligomer, formed from one compound according to the invention and at least one other compound joined together via a linker linked to element A. Preferably the linker is selected from the group comprising nucleotide linkers, polyethylene glycols, peptide linkers and/or linear or branched, saturated or unsaturated $C_1$-$C_{50}$-alkyl.

Preferably, a nucleotide linker has a length in the range of ≥1 nucleotide to ≤30 nucleotides, preferred in the range of ≥2 nucleotides to ≤15 nucleotides, further preferred in the range of ≥5 nucleotides to ≤15 nucleotides, more preferred in the range of ≥10 nucleotides to ≤15 nucleotides, wherein the nucleotides are selected from the group comprising guanosine, cytidine, adenosine and/or thymidine. A preferred nucleotide is adenosine. Especially preferred linkers are Poly A-linkers. Preferably, a polyethylene glycol linker comprises 1 to 15 polyethylene glycol units, preferred in the range of 1 to 10 polyethylene glycol units, more preferred in the range of 2 to 8 polyethylene glycol units. Preferred are linear polyethylene glycol (PEG) units HO—(CH₂CH₂O)$_n$—H, wherein n is an integer in the range of 1 to 15, preferred in the range of 1 to 10, more preferred in the range of 2 to 8. In preferred embodiments the linker is a peptide linker, wherein the peptide linker preferably comprises amino acids selected from the group comprising glycine, alanine and/or β-alanine. Preferably, the peptide linker comprises in the range of 2 to 4 amino acids. Preferably, the peptide linker comprises β-β-alanine units. Preferably, the peptide linker comprises in the range of 2 to 4 β-alanine units. In preferred embodiments the linker is a linear or branched, saturated or unsaturated $C_1$-$C_{40}$-alkyl group, preferred a $C_1$-$C_{30}$ alkyl group, more preferred a $C_2$-$C_{20}$-alkyl group Preferably, the linker is an alkyl group —(CH₂)$_n$— wherein n is an integer in the range of 1 to 40, preferred in the range of 1 to 30, further preferred in the range of 2 to 20, more preferred in the range of 2 to 18, even more preferred n is 2, 6, 12 or 18.

A further aspect of the present invention relates to a pharmaceutical composition comprising as an active ingredient a compound according to general formula (I) as given as follows and/or racemates, enantiomers, diastereomers, solvates, hydrates, and pharmaceutically acceptable salts and/or esters thereof:

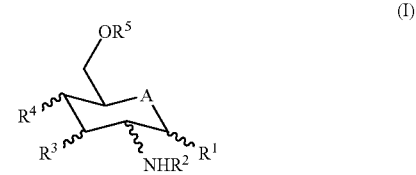

(I)

wherein:

$R^1$ is selected from the group comprising H, OH, SH and/or NH₂;

$R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, C(O)$C_1$-$C_{10}$-alkyl, OC(O)$C_1$-$C_{10}$-alkyl, C(O)O$C_1$-$C_{10}$-alkyl, C(O)NH₂, NH₂ and/or S(O)₂OH;

$R^3$ is selected from the group comprising OH, SH and/or NH₂;

$R^4$ is selected from the group comprising OH, SH and/or NH₂;

$R^5$ is selected from the group comprising hydrogen, P(O)(OH)₂, S(O)₂OH, P(S)(OH)₂, P(O)OHSH, S(O)₂SH and/or aryloxy phosphoramidates according to general formula (II)

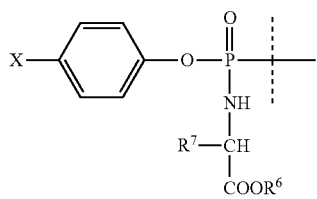

(II)

wherein:
R⁶ is selected from the group comprising linear or branched $C_1$-$C_6$-alkyl, benzyl and/or cyclohexyl;
R⁷ is a side chain of an amino acid selected from the group comprising hydrogen; linear or branched $C_1$-$C_4$-alkyl; linear or branched alkyl groups of the type —$C_nH_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$—$C_6H_4$—Y wherein Y is selected from the group comprising OH, SH, $C_1$-$C_3$-alkyl and/or $NH_2$; —$CH_2$-imidazole; —$CH_2$-indole; —$CH_2$-(furanyl-3-yl); —$CH_2$-(pyridyl-3-yl) and/or —$CH_2$— (imidazolyl-3-yl);
X is selected from the group comprising Cl, Br, I, $C_1$-$C_6$-alkyl and/or $C_1$-$C_6$-alkoxy;
A is selected from the group comprising S, NR⁸, C=CR⁸R⁹ and/or CR⁸R⁹, wherein
R⁸, R⁹ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker.

Preferably, the substituent A is selected from the group comprising S, NR⁸ and/or CR⁸R⁹, wherein R⁸ and R⁹ are selected, the same or each independently of the other, from the group comprising hydrogen, $C_1$-$C_5$-alkyl; $C_6$-$C_{10}$-aryl, or $C_2$-$C_5$-alkenyl. In a preferred embodiment, the element A is a group —$CH_2$— and the compound has the formula (III) as indicated below and/or racemates, enantiomers, diastereomers, solvates, hydrates, and pharmaceutically acceptable salts and/or esters thereof:

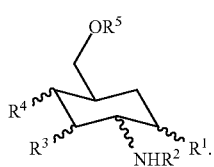

(III)

Preferably, the substituent R¹ is a hydroxyl group. Further, the substituent R¹ can be hydrogen. Further preferred, the substituent R³ is a hydroxyl group. Further preferred, the substituent R⁴ is a hydroxyl group. In a preferred embodiment of the compound according to the invention the substituents R¹, R³ and R⁴ are OH. In another preferred embodiment of the compound according to the invention the substituent R¹ is hydrogen and the substituents R³ and R⁴ are OH.

In a preferred embodiment, the substituent R² is selected from the group comprising hydrogen, $C_1$-$C_5$-alkyl preferably methyl, ethyl or n-propyl, benzyl, $C_1$-$C_5$-acyl preferably $C(O)CH_3$, $C(O)C_2H_5$, C(O)n-propyl or C(O)iso-propyl, $C_1$-$C_5$-alkylester preferably $OC(O)CH_3$, $OC(O)C_2H_5$, OC(O)n-propyl or OC(O)iso-propyl, $C(O)NH_2$, $NH_2$ and/or $S(O)_2OH$. Most preferred, the substituent R² is hydrogen. Further preferred, the substituent R² is selected from the group comprising $C_1$-$C_5$-alkyl preferably methyl, ethyl or n-propyl, benzyl, $C_1$-$C_5$-acyl preferably $C(O)CH_3$, $C(O)C_2H_5$, C(O)n-propyl or C(O)iso-propyl, $C_1$-$C_5$-alkylester preferably $OC(O)CH_3$, $OC(O)C_2H_5$, OC(O)n-propyl or OC(O)iso-propyl, $C(O)NH_2$, $NH_2$ and/or $S(O)_2OH$. Preferred are small alkyl, acyl and ester groups selected from methyl, ethyl, $C(O)CH_3$, $C(O)C_2H_5$, $OC(O)CH_3$, $OC(O)C_2H_5$, and benzyl. It is also preferred that the substituent R² is selected from $C(O)NH_2$, $NH_2$ or $S(O)_2OH$.

Preferably, the substituent R⁵ is selected from the group comprising hydrogen, $P(O)(OH)_2$ and/or aryloxy phosphoramidates according to formula (II) wherein R⁶ is selected from the group comprising methyl, ethyl, isopropyl, cyclohexyl and benzyl, X is methoxy and R⁷ is methyl or another side chain of an amino acid. Preferably, the substituent R⁵ is hydrogen. Most preferred, the substituent R⁵ is $P(O)(OH)_2$. Further preferred, the substituent R⁵ is an aryloxy phosphoramidate according to formula (II). Preferred are aryloxy phosphoramidates wherein R⁶ is methyl, ethyl, isopropyl, cyclohexyl or benzyl, X is methoxy and R⁷ is methyl or another side chain of an amino acid.

The substituent R⁷ is a side chain of an amino acid. Preferably, the substituent R⁷ is a side chain of a naturally occurring amino acid selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline, preferably alanine, phenylalanine, proline, valine, leucine, isoleucine, glycine, methionine, or α,α-dimethylglycine. In preferred embodiments, the substituent R⁷ is a linear or branched alkyl groups of the type —$C_nH_{2n}$-U-D wherein n is 1, 2, 3 or 4, U is selected from the group comprising O, CO, COO, CONH, S, guanidine and/or NH, and D is selected from the group comprising H and/or methyl; —$CH_2$—$C_6H_4$—OH; —$CH_2$-imidazole and/or —$CH_2$-indole. Preferably, the substituent R⁷ is a side chain of an amino acid selected from the group comprising hydrogen; linear or branched $C_1$-$C_4$-alkyl, most preferred methyl.

In a preferred embodiment, the substituent R⁵ is selected from the group comprising hydrogen, $P(O)(OH)_2$ and/or aryloxy phosphoramidates according to formula (II) wherein R⁶ is methyl, ethyl, isopropyl, cyclohexyl or benzyl, X is methoxy and R⁷ is methyl.

In especially preferred embodiments, the compound is selected from the group comprising the formulas (1), (2), (3) and/or (4) as indicated above and/or racemates, enantiomers, diastereomers, solvates, hydrates, and pharmaceutically acceptable salts and/or esters thereof.

In an especially preferred embodiment, the pharmaceutical composition comprises a compound selected from the group comprising the formulas (1) and/or (2) as indicated above and/or racemates, enantiomers, diastereomers, solvates, hydrates, and pharmaceutically acceptable salts and/or esters thereof. In a further especially preferred embodiment, the pharmaceutical composition comprises a compound selected from the group comprising the formulas (1) and/or (2) as indicated above and/or racemates, enantiomers, diastereomers, solvates, hydrates, and pharmaceutically acceptable salts and/or esters thereof.

Further preferred, the compound according to general formula (I) can be part of a dimer, trimer or oligomer, formed from one compound according to the invention and at least one other compound joined together via a linker linked to element A. Preferably the linker is selected from the group comprising nucleotide linkers, polyethylene glycols, peptide linkers and/or linear or branched, saturated or unsaturated $C_1$-$C_{50}$-alkyl.

Preferably, a nucleotide linker has a length in the range of ≥1 nucleotide to ≤30 nucleotides, preferred in the range of ≥2 nucleotides to ≤15 nucleotides, further preferred in the range of ≥5 nucleotides to ≤15 nucleotides, more preferred in the range of ≥10 nucleotides to ≤15 nucleotides, wherein the nucleotides are selected from the group comprising guanosine, cytidine, adenosine and/or thymidine. A preferred nucleotide is adenosine. Especially preferred linkers are Poly A-linkers. Preferably, a polyethylene glycol linker comprises 1 to 15 polyethylene glycol units, preferred in the range of 1 to 10 polyethylene glycol units, more preferred in the range of 2 to 8 polyethylene glycol units. Preferred are linear polyethylene glycol (PEG) units HO—$(CH_2CH_2O)_n$—H, wherein n is an integer in the range of 1 to 15, preferred in the range of 1 to 10, more preferred in the range of 2 to 8. In preferred embodiments the linker is a peptide linker, wherein the peptide linker preferably comprises amino acids selected from the group comprising glycine, alanine and/or β-alanine. Preferably, the peptide linker comprises in the range of 2 to 4 amino acids. Preferably, the peptide linker comprises β-β-alanine units. Preferably, the peptide linker comprises in the range of 2 to 4 β-alanine units. In preferred embodiments the linker is a linear or branched, saturated or unsaturated $C_1$-$C_{40}$-alkyl group, preferred a $C_1$-$C_{30}$ alkyl group, more preferred a $C_2$-$C_{20}$-alkyl group Preferably, the linker is an alkyl group —$(CH_2)_n$— wherein n is an integer in the range of 1 to 40, preferred in the range of 1 to 30, further preferred in the range of 2 to 20, more preferred in the range of 2 to 18, even more preferred n is 2, 6, 12 or 18.

A further aspect of the present invention relates to a pharmaceutical composition comprising as an active ingredient a compound according to general formula (I) as given as above and/or racemates, enantiomers, diastereomers, solvates, hydrates, and pharmaceutically acceptable salts and/or esters thereof for use in the therapeutic and/or prophylactic treatment of a bacterial infection, particularly for use as an antibiotic. Preferably, the pharmaceutical composition for use in the therapeutic and/or prophylactic treatment of a bacterial infection, particularly for use as an antibiotic comprises a compound selected from the group comprising the formulas (1), (2), (3) and/or (4) as indicated above and/or racemates, enantiomers, diastereomers, solvates, hydrates, and pharmaceutically acceptable salts and/or esters thereof. The pharmaceutical composition preferably is useful as an antibiotic.

The present invention also relates to an antibiotic comprising, as an active ingredient, a compound according to general formula (I) as given as follows and/or racemates, enantiomers, diastereomers, solvates, hydrates, and pharmaceutically acceptable salts and/or esters thereof:

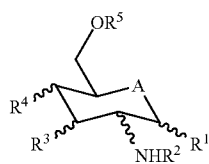

(I)

wherein:

$R^1$ is selected from the group comprising H, OH, SH and/or $NH_2$;

$R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;

$R^3$ is selected from the group comprising OH, SH and/or $NH_2$;

$R^4$ is selected from the group comprising OH, SH and/or $NH_2$;

$R^5$ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

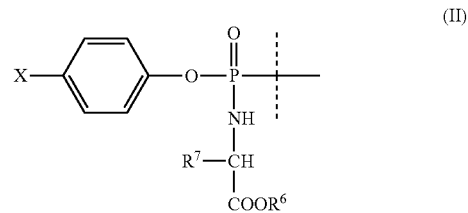

(II)

wherein:

$R^6$ is selected from the group comprising linear or branched $C_1$-$C_6$-alkyl, benzyl and/or cyclohexyl;

$R^7$ is a side chain of an amino acid selected from the group comprising hydrogen; linear or branched $C_1$-$C_4$-alkyl; linear or branched alkyl groups of the type —$C_nH_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$—$C_6H_4$—Y wherein Y is selected from the group comprising OH, SH, $C_1$-$C_3$-alkyl and/or $NH_2$; —$CH_2$-imidazole; —$CH_2$-indole; —$CH_2$-(furanyl-3-yl); —$CH_2$-(pyridyl-3-yl) and/or —$CH_2$— (imidazolyl-3-yl);

X is selected from the group comprising Cl, Br, I, $C_1$-$C_6$-alkyl and/or $C_1$-$C_6$-alkoxy;

A is selected from the group comprising S, $NR^8$, C=$CR^8R^9$ and/or $CR^8R^9$, wherein $R^8$, $R^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker.

Preferably, the substituent A is selected from the group comprising S, $NR^8$ and/or $CR^8R^9$, wherein $R^8$ and $R^9$ are selected, the same or each independently of the other, from the group comprising hydrogen, $C_1$-$C_5$-alkyl, $C_6$-$C_{10}$-aryl, or $C_2$-$C_5$-alkenyl. In a preferred embodiment, the element A is a group —$CH_2$— and the compound has the formula (III) as indicated below and/or racemates, enantiomers, diastereomers, solvates, hydrates, and pharmaceutically acceptable salts and/or esters thereof:

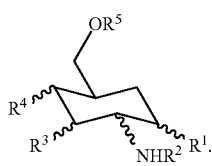

(III)

Preferably, the substituent $R^1$ is a hydroxyl group. Further, the substituent $R^1$ can be hydrogen. Further preferred, the substituent $R^3$ is a hydroxyl group. Further preferred, the substituent $R^4$ is a hydroxyl group. In a preferred embodiment of the compound according to the invention the substituents $R^1$, $R^3$ and $R^4$ are OH. In another preferred embodiment of the compound according to the invention the substituent $R^1$ is hydrogen and the substituents $R^3$ and $R^4$ are OH.

In a preferred embodiment, the substituent $R^2$ is selected from the group comprising hydrogen, $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Most preferred, the substituent $R^2$ is hydrogen. Further preferred, the substituent $R^2$ is selected from the group comprising $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Preferred are small alkyl, acyl and ester groups selected from methyl, ethyl, $C(O)CH_3$, $C(O)C_2H_5$, $OC(O)CH_3$, $OC(O)C_2H_5$, and benzyl. It is also preferred that the substituent $R^2$ is selected from $C(O)NH_2$, $NH_2$ or $S(O)_2OH$.

Preferably, the substituent $R^5$ is selected from the group comprising hydrogen, $P(O)(OH)_2$ and/or aryloxy phosphoramidates according to formula (II) wherein $R^6$ is selected from the group comprising methyl, ethyl, isopropyl, cyclohexyl and benzyl, X is methoxy and $R^7$ is methyl or another side chain of an amino acid. Preferably, the substituent $R^5$ is hydrogen. Most preferred, the substituent $R^5$ is $P(O)(OH)_2$. Further preferred, the substituent $R^5$ is an aryloxy phosphoramidate according to formula (II). Preferred are aryloxy phosphoramidates wherein $R^6$ is methyl, ethyl, isopropyl, cyclohexyl or benzyl, X is methoxy and $R^7$ is methyl or another side chain of an amino acid.

The substituent $R^7$ is a side chain of an amino acid. Preferably, the substituent $R^7$ is a side chain of a naturally occurring amino acid selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline, preferably alanine, phenylalanine, proline, valine, leucine, isoleucine, glycine, methionine, or α,α-dimethylglycine. In preferred embodiments, the substituent $R^7$ is a linear or branched alkyl groups of the type —$C_nH_{2n}$-U-D wherein n is 1, 2, 3 or 4, U is selected from the group comprising O, CO, COO, CONH, S, guanidine and/or NH, and D is selected from the group comprising H and/or methyl; —$CH_2$—$C_6H_4$—OH; —$CH_2$-imidazole and/or —$CH_2$-indole. Preferably, the substituent $R^7$ is a side chain of an amino acid selected from the group comprising hydrogen; linear or branched $C_1$-$C_4$-alkyl, most preferred methyl.

In a preferred embodiment, the substituent $R^5$ is selected from the group comprising hydrogen, $P(O)(OH)_2$ and/or aryloxy phosphoramidates according to formula (II) wherein $R^6$ is methyl, ethyl, isopropyl, cyclohexyl or benzyl, X is methoxy and $R^7$ is methyl.

In a preferred embodiment, the antibiotic comprises compound according to general formula (I) comprising an element A being a group —$CH_2$—, the substituents $R^1$, $R^3$, and $R^4$ being OH, $R^2$ is hydrogen or $C(O)CH_3$, and $R^5$ is hydrogen or $P(O)(OH)_2$.

Preferably, the present invention relates to a pharmaceutical composition comprising as an active ingredient compounds according to the formulas (1), (2), (3) and/or (4) as indicated above and/or racemates, enantiomers, diastereomers, solvates, hydrates, and pharmaceutically acceptable salts and/or esters thereof. In a preferred embodiment, the antibiotic comprises as an active ingredient compounds according to the formulas (1), (2), (3) and/or (4) as indicated above and/or racemates, enantiomers, diastereomers, solvates, hydrates, and pharmaceutically acceptable salts and/or esters thereof. Especially, the compounds according to formulas (1) and (3) were found to effectively inhibit bacterial growth of *Staphylococcus aureus*.

Further preferred, the compound according to general formula (I) can be part of a dimer, trimer or oligomer, formed from one compound according to the invention and at least one other compound joined together via a linker linked to element A. Preferably the linker is selected from the group comprising nucleotide linkers, polyethylene glycols, peptide linkers and/or linear or branched, saturated or unsaturated $C_1$-$C_{50}$-alkyl.

Preferably, a nucleotide linker has a length in the range of ≥1 nucleotide to ≤30 nucleotides, preferred in the range of ≥2 nucleotides to ≤15 nucleotides, further preferred in the range of ≥5 nucleotides to ≤15 nucleotides, more preferred in the range of ≥10 nucleotides to ≤15 nucleotides, wherein the nucleotides are selected from the group comprising guanosine, cytidine, adenosine and/or thymidine. A preferred nucleotide is adenosine. Especially preferred linkers are Poly A-linkers. Preferably, a polyethylene glycol linker comprises 1 to 15 polyethylene glycol units, preferred in the range of 1 to 10 polyethylene glycol units, more preferred in the range of 2 to 8 polyethylene glycol units. Preferred are linear polyethylene glycol (PEG) units HO—$(CH_2CH_2O)_n$—H, wherein n is an integer in the range of 1 to 15, preferred in the range of 1 to 10, more preferred in the range of 2 to 8. In preferred embodiments the linker is a peptide linker, wherein the peptide linker preferably comprises amino acids selected from the group comprising glycine, alanine and/or β-alanine. Preferably, the peptide linker comprises in the range of 2 to 4 amino acids. Preferably, the peptide linker comprises β-β-alanine units. Preferably, the peptide linker comprises in the range of 2 to 4 β-alanine units. In preferred embodiments the linker is a linear or branched, saturated or unsaturated $C_1$-$C_{40}$-alkyl group, preferred a $C_1$-$C_{30}$ alkyl group, more preferred a $C_2$-$C_{20}$-alkyl group Preferably, the linker is an alkyl group —$(CH_2)_n$— wherein n is an integer in the range of 1 to 40, preferred in the range of 1 to 30, further preferred in the range of 2 to 20, more preferred in the range of 2 to 18, even more preferred n is 2, 6, 12 or 18.

The compounds and/or racemates, enantiomers, diastereomers, solvates, hydrates, and pharmaceutically acceptable salts and/or esters thereof can be included in pharmaceutical compositions in combination with one or more other therapeutically active compounds. The pharmaceutical composition particularly is usable as an antibiotic.

Further, the compounds according to the present invention are usable in form of solvates, hydrates, and pharmaceutically acceptable salts and/or esters thereof.

Usable are pharmaceutically acceptable salts of the compounds according to the present invention. The term "pharmaceutically acceptable salts" refers to salts prepared from pharmaceutically acceptable non-toxic bases or acids.

When the compound of the present invention is acidic, its corresponding salt can be conveniently prepared from pharmaceutically acceptable non-toxic bases, including inorganic bases and organic bases. Preferred salts derived from inorganic bases include ammonium, calcium, magnesium, potassium and sodium salts. Salts derived from pharmaceutically acceptable organic non-toxic bases include salts of primary, secondary, and tertiary amines, as well as cyclic amines.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

Further usable are pharmaceutically acceptable esters of the compounds according to the present invention. The term "pharmaceutically acceptable ester" refers to esters prepared from pharmaceutically acceptable non-toxic ester groups. Most preferred the substituent $R^2$ is an acetyl group.

Preferably, the pharmaceutical composition comprises a compound according to the invention and/or racemates, enantiomers, diastereomers, solvates, hydrates, and pharmaceutically acceptable salts and/or esters thereof as an active ingredient, a pharmaceutically acceptable carrier and optionally other therapeutic ingredients or adjuvants.

The pharmaceutical carrier can be, for example, a solid, liquid, or gas. Suitable carriers and adjuvants can be solid or liquid and correspond to the substances ordinarily employed in formulation technology for pharmaceutical formulations. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

The compositions can be suitable for oral, dermal, rectal, topical, and parenteral administration. Parenteral administration includes subcutaneous, intramuscular, and intravenous administration. The pharmaceutical compositions may be conveniently presented in unit dosage form and prepared by any of the methods well known in the art of pharmacy.

The pharmaceutical composition of the present invention can be presented as discrete unit suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. Further, the pharmaceutical composition may be administered by controlled release means and/or delivery devices.

For compositions for oral dosage form, convenient pharmaceutical media may be employed. For example, water, glycols, oils, alcohols, flavouring agents, preservatives, colouring agents and the like may be used to form oral liquid preparations such as solutions. Carriers such as starches, sugars, microcrystalline cellulose, diluents, granulating agents, lubricants, binders, disintegrating agents, and the like may be used to form oral solid preparations such as powders, capsules and tablets. Optionally, tablets may be coated by standard aqueous or non aqueous techniques.

Pharmaceutical compositions of the present invention suitable for parenteral administration may be prepared as solutions or suspensions of the active compounds in water. A suitable excipient can be included such as, for example, hydroxypropylcellulose. Dispersions can also be prepared in glycerol, liquid polyethylene glycols, and mixtures thereof in oils. Pharmaceutical compositions of the present invention suitable for injectable use include sterile aqueous solutions or dispersions. Further, a preservative can be included to prevent the growth of microorganisms.

The pharmaceutical compositions of the present invention can be in a form suitable for topical use such as, for example, an aerosol, cream, ointment, lotion, dusting powder, or the like. Further, the compositions can be in a form suitable for use in transdermal devices. The pharmaceutical composition may also be prepared in powder or liquid concentrate form. The pharmaceutical composition of the present invention can include one or more additional carrier ingredients such as diluents, buffers, flavouring agents, binders, surface-active agents, thickeners, lubricants, preservatives and the like.

The pharmaceutical composition of the present invention can comprise a compound according to general formula (I) alone or in combination with other antibiotics. The invention further relates to a pharmaceutical composition comprising as an active ingredient a combination of a compound according to general formula (I) as given above and/or racemates, enantiomers, diastereomers, solvates, hydrates, and pharmaceutically acceptable salts and/or esters thereof, and vancomycin. Preferably, the pharmaceutical composition comprises a combination of vancomycin and a compound according to general formula (I), wherein element A is a group —$CH_2$—, the substituents $R^1$, $R^3$, and $R^4$ are OH, $R^2$ is hydrogen or $C(O)CH_3$, and $R^5$ is hydrogen or $P(O)(OH)_2$. Preferably, the pharmaceutical composition comprises a combination of vancomycin and a compound selected from the group comprising the formulas (1), (2), (3) and/or (4) as indicated above and/or racemates, enantiomers, diastereomers, solvates, hydrates, and pharmaceutically acceptable salts and/or esters thereof.

The pharmaceutical composition may be produced under sterile conditions using standard pharmaceutical techniques well known to those skilled in the art.

The present invention also relates to the use of a compound according to general formula (I) as given as follows and/or racemates, enantiomers, diastereomers, solvates, hydrates, and pharmaceutically acceptable salts and/or esters thereof:

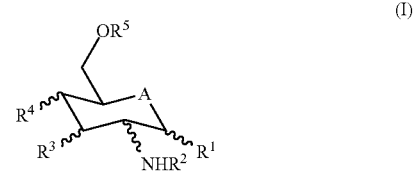

(I)

wherein:
$R^1$ is selected from the group comprising H, OH, SH and/or $NH_2$;
$R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;

$R^3$ is selected from the group comprising OH, SH and/or $NH_2$;

$R^4$ is selected from the group comprising OH, SH and/or $NH_2$;

$R^5$ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

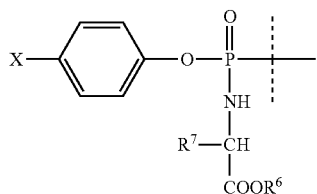
(II)

wherein:

$R^6$ is selected from the group comprising linear or branched $C_1$-$C_6$-alkyl, benzyl and/or cyclohexyl;

$R^7$ is a side chain of an amino acid selected from the group comprising hydrogen; linear or branched $C_1$-$C_4$-alkyl; linear or branched alkyl groups of the type —$C_nH_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$—$C_6H_4$—Y wherein Y is selected from the group comprising OH, SH, $C_1$-$C_3$-alkyl and/or $NH_2$; —$CH_2$-imidazole; —$CH_2$-indole; —$CH_2$-(furanyl-3-yl); —$CH_2$-(pyridyl-3-yl) and/or —$CH_2$— (imidazolyl-3-yl);

X is selected from the group comprising Cl, Br, I, $C_1$-$C_6$-alkyl and/or $C_1$-$C_6$-alkoxy;

A is selected from the group comprising S, $NR^8$, C=$CR^8R^9$ and/or $CR^8R^9$, wherein $R^8$, $R^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2$OH and/or a linker;

for the manufacture of a medicament.

The present invention also relates to the use of a compound according to general formula (I) as given above for the manufacture of a medicament for the therapeutic and/or prophylactic treatment of a bacterial infection, particularly for the manufacture of an antibiotic.

It is a particular advantage of the compounds according to the invention is that the compounds are especially usable for the manufacture of an antibiotic, particularly against the multiresistant *Staphylococcus aureus* strain.

Preferably, the substituent A is selected from the group comprising S, $NR^8$ and/or $CR^8R^9$, wherein $R^8$ and $R^9$ are selected, the same or each independently of the other, from the group comprising hydrogen, $C_1$-$C_5$-alkyl, $C_6$-$C_{10}$-aryl, or $C_2$-$C_5$-alkenyl. In a preferred embodiment, the element A is a group —$CH_2$— and the compound has the formula (III) as indicated below and/or racemates, enantiomers, diastereomers, solvates, hydrates, and pharmaceutically acceptable salts and/or esters thereof:

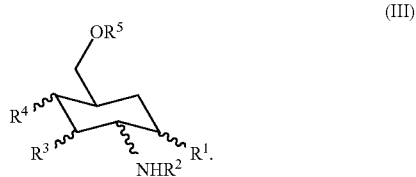
(III)

Preferably, the substituent $R^1$ is a hydroxyl group. Further, the substituent $R^1$ can be hydrogen. Further preferred, the substituent $R^3$ is a hydroxyl group. Further preferred, the substituent $R^4$ is a hydroxyl group. In a preferred embodiment of the compound according to the invention the substituents $R^1$, $R^3$ and $R^4$ are OH. In another preferred embodiment of the compound according to the invention the substituent $R^1$ is hydrogen and the substituents $R^3$ and $R^4$ are OH.

In a preferred embodiment, the substituent $R^2$ is selected from the group comprising hydrogen, $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Most preferred, the substituent $R^2$ is hydrogen. Further preferred, the substituent $R^2$ is selected from the group comprising $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C_1$-$C_5$-alkylester preferably $OC(O)CH_3$, $OC(O)C_2H_5$, $OC(O)$n-propyl or $OC(O)$iso-propyl, $C(O)NH_2$, $NH_2$ and/or $S(O)_2OH$. Preferred are small alkyl, acyl and ester groups selected from methyl, ethyl, $C(O)CH_3$, $C(O)C_2H_5$, $OC(O)CH_3$, $OC(O)C_2H_5$, and benzyl. It is also preferred that the substituent $R^2$ is selected from $C(O)NH_2$, $NH_2$ or $S(O)_2OH$.

Preferably, the substituent $R^5$ is selected from the group comprising hydrogen, $P(O)(OH)_2$ and/or aryloxy phosphoramidates according to formula (II) wherein $R^6$ is selected from the group comprising methyl, ethyl, isopropyl, cyclohexyl and benzyl, X is methoxy and $R^7$ is methyl or another side chain of an amino acid. Preferably, the substituent $R^5$ is hydrogen. Most preferred, the substituent $R^5$ is $P(O)(OH)_2$. Further preferred, the substituent $R^5$ is an aryloxy phosphoramidate according to formula (II). Preferred are aryloxy phosphoramidates wherein $R^6$ is methyl, ethyl, isopropyl, cyclohexyl or benzyl, X is methoxy and $R^7$ is methyl or another side chain of an amino acid.

The substituent $R^7$ is a side chain of an amino acid. Preferably, the substituent $R^7$ is a side chain of a naturally occurring amino acid selected from the group comprising glycine, alanine, serine, threonine, arginine, lysine, aspartic acid, glutamic acid, asparagine, glutamine, phenylalanine, tyrosine, tryptophan, leucine, valine, isoleucine, cysteine, methionine, histidine and/or proline, preferably alanine, phenylalanine, proline, valine, leucine, isoleucine, glycine, methionine, or α,α-dimethylglycine. In preferred embodiments, the substituent $R^7$ is a linear or branched alkyl groups of the type —$C_nH_{2n}$-U-D wherein n is 1, 2, 3 or 4, U is selected from the group comprising O, CO, COO, CONH, S, guanidine and/or NH, and D is selected from the group comprising H and/or methyl; —$CH_2$—$C_6H_4$—OH; —$CH_2$-imidazole and/or —$CH_2$-indole. Preferably, the substituent $R^7$ is a side chain of an amino acid selected from the group comprising hydrogen; linear or branched $C_1$-$C_4$-alkyl, most preferred methyl.

In a preferred embodiment, the substituent $R^5$ is selected from the group comprising hydrogen, $P(O)(OH)_2$ and/or aryloxy phosphoramidates according to formula (II) wherein $R^6$ is methyl, ethyl, isopropyl, cyclohexyl or benzyl, X is methoxy and $R^7$ is methyl.

In especially preferred embodiments, the compound is selected from the group comprising the formulas (1), (2), (3) and/or (4) as indicated above and/or racemates, enantiomers, diastereomers, solvates, hydrates, and pharmaceutically acceptable salts and/or esters thereof.

Preferably, for the manufacture of a medicament the compound is selected from the group comprising the formulas (1) and/or (2) as indicated above and/or racemates, enantiomers, diastereomers, solvates, hydrates, and pharmaceutically acceptable salts and/or esters thereof. Preferably, for the manufacture of a medicament for the therapeutic and/or prophylactic treatment of a bacterial infection, particularly for the manufacture of an antibiotic the compound is selected from the group comprising the formulas (1), (2), (3) and/or (4) as indicated above and/or racemates, enantiomers, diastereomers, solvates, hydrates, and pharmaceutically acceptable salts and/or esters thereof.

Further preferred, the compound according to general formula (I) can be part of a dimer, trimer or oligomer, formed from one compound according to the invention and at least one other compound joined together via a linker linked to element A. Preferably the linker is selected from the group comprising nucleotide linkers, polyethylene glycols, peptide linkers and/or linear or branched, saturated or unsaturated $C_1$-$C_{50}$-alkyl.

Preferably, a nucleotide linker has a length in the range of ≥1 nucleotide to ≤30 nucleotides, preferred in the range of ≥2 nucleotides to ≤15 nucleotides, further preferred in the range of ≥5 nucleotides to ≤15 nucleotides, more preferred in the range of ≥10 nucleotides to ≤15 nucleotides, wherein the nucleotides are selected from the group comprising guanosine, cytidine, adenosine and/or thymidine. A preferred nucleotide is adenosine. Especially preferred linkers are Poly A-linkers. Preferably, a polyethylene glycol linker comprises 1 to 15 polyethylene glycol units, preferred in the range of 1 to 10 polyethylene glycol units, more preferred in the range of 2 to 8 polyethylene glycol units. Preferred are linear polyethylene glycol (PEG) units HO—$(CH_2CH_2O)_n$—H, wherein n is an integer in the range of 1 to 15, preferred in the range of 1 to 10, more preferred in the range of 2 to 8. In preferred embodiments the linker is a peptide linker, wherein the peptide linker preferably comprises amino acids selected from the group comprising glycine, alanine and/or β-alanine. Preferably, the peptide linker comprises in the range of 2 to 4 amino acids. Preferably, the peptide linker comprises β-β-alanine units. Preferably, the peptide linker comprises in the range of 2 to 4 β-alanine units. In preferred embodiments the linker is a linear or branched, saturated or unsaturated $C_1$-$C_{40}$-alkyl group, preferred a $C_1$-$C_{30}$ alkyl group, more preferred a $C_2$-$C_{20}$-alkyl group Preferably, the linker is an alkyl group —$(CH_2)_n$— wherein n is an integer in the range of 1 to 40, preferred in the range of 1 to 30, further preferred in the range of 2 to 20, more preferred in the range of 2 to 18, even more preferred n is 2, 6, 12 or 18.

The compounds of the present invention can be used alone or in combination with other antibiotics. The invention further relates to the use of a compound according to general formula (I) as given above and vancomycin for the manufacture of a medicament for the therapeutic and/or prophylactic treatment of a bacterial infection, particularly for the manufacture of an antibiotic. Preferably, the element A is a group —$CH_2$—, the substituents $R^1$, $R^3$, and $R^4$ are OH, $R^2$ is hydrogen or $C(O)CH_3$, and $R^5$ is hydrogen or $P(O)(OH)_2$, more preferably, the compound is selected from the group comprising the formulas (1), (2), (3) and/or (4) as indicated above and/or racemates, enantiomers, diastereomers, solvates, hydrates, and pharmaceutically acceptable salts and/or esters thereof.

The compounds of the present invention may be prepared using a variety of processes well known by a person skilled in the art.

A further aspect of the present invention relates to a method for the preparation of phosphorylated compounds according to the invention.

In a preferred embodiment, the compounds according to the invention wherein $R^5$ is $P(O)(OH)_2$ may be prepared by a method comprising the steps of:
a) Providing or Preparation of a cyclohexane according to formula (IV)

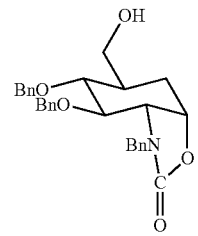

(IV)

b) Alkaline hydrolysis of the carbamate moiety to a 1-hydroxy-2-benzylamino moiety;
c) Selective introduction of a phosphate group to the primary hydroxyl group of the hydrolysed cyclohexane of step b);
d) Reduction of the benzyl protecting groups to the respective alcohol and amine groups of the cyclohexane of step c).

The cyclohexane according to formula (IV) may be prepared using processes well known by a person skilled in the art. The term "Bn" denotes a benzyl group for the protection of the respective alcohol and amine groups.

The alkaline hydrolysis of the alkyl ester of the carbamate moiety to a 1-hydroxy-2-benzylamino moiety of step b) preferably is carried out in the presence of NaOH. A preferred solvent is a mixture of ethanol and NaOH, preferably a 1:1 mixture of ethanol and 2 N NaOH.

In step c) a phosphate group is introduced to the primary hydroxyl group of the hydrolysed cyclohexane of step b). The phosphorylation preferably is carried out using phosphoryl chloride ($POCl_3$), pyridine, and water in acetonitrile ($CH_3CN$).

The reduction of the benzyl protecting groups to the respective alcohol and amine groups of the cyclohexane of step c) in step d) preferably is carried out by catalytic hydrogenation with palladium on carbon as a catalyst. A preferred solvent for the reduction is methanol.

Upon reduction of the benzyl groups to the respective alcohol and amine groups of the cyclohexane of step c) after introduction of a phosphate group to the primary hydroxyl group of the hydrolysed cyclohexane a phosphorylated cyclohexane is received, as for example the compound according to formula (1).

The examples which follow serve to illustrate the invention in more detail but do not constitute a limitation thereof.

Unless stated otherwise, a purification of compounds was carried out using flash column chromatography, a variant of column chromatography. Flash column chromatography was carried out using Merck silica gel 60 (40-63 μm). Pressure was achieved by nitrogen. The mobile phase, column diameter (Ø), filling level of silica gel, and volume of fractions was adjusted to experimental conditions.

The solvents were distilled before used. Chemicals were purchased from Acros, Fluka, Merck, Sigma-Aldrich, Fisher Scientific and Glycon and used without further purification, unless stated otherwise.

The compound according to formula (3) was prepared according to the procedure according to Miyamoto, M. et al., Tetrahedron Lett. 1992, 33, 3725-3728.

EXAMPLE 1

Preparation of the Compound According to Formula (1) (1S,2S,3R,4R,5R)-2-amino-5-((phosphonooxy) methyl)-cyclohexane-1,3,4-triol step 1.1 Preparation of (1S,2S,3R,4R,5R)-3,4-di-O-benzyl-2-benzylamino-1,2-N,O-carbonyl-5-hydroxymethyl-cyclohexane-1,3,4-triole (1S,2S,3R,4R,5R)-3,4-di-O-benzyl-2-benzylamino-1,2-N,O-carbonyl-5-hydroxymethyl-cyclohexane-1,3,4-triole was prepared according to the method of Barton et al., Tetrahedron 1990, 46, 215-230, in ten reaction steps.

step 1.2 Preparation of (1S,2S,3R,4R,5R)-3,4-di-O-benzyl-2-benzylamino-5-hydroxymethyl-cyclohexane-1,3,4-triole 580 mg of (1S,2S,3R,4R,5R)-3,4-di-O-benzyl-2-benzylamino-1,2-N,O-carbonyl-5-hydroxymethyl-cyclohexane-1,3,4-triole of step 1.1 (1.23 mmol) was dissolved in 30 mL EtOH/2N NaOH (1:1) and stirred for 14 h under reflux. The mixture was diluted with water and extracted with EtOAc (2×50 mL). The organic layer was dried ($Na_2SO_4$) and the solvent was evaporated. Purification by flash column chromatography (petroleum ether/EtOAc 1:1) yielded the titled compound (400 mg, 73%) as a colorless solid.

step 1.3 Preparation of (1S,2S,3R,4R,5R)-3,4-di-O-benzyl-2-benzylamino-5-((phosphonooxy)methyl)-cyclohexane-1,3,4-triol 160 µL $POCl_3$ (1.74 mmol), 24 µL $H_2O$ (1.34 mmol), and 149 µL pyridine (1.85 mmol) were dissolved in acetonitrile (2 mL) and stirred for 10 min at 0° C. 150 mg of the compound of step 1.2 (0.34 mmol) was added and the mixture was stirred for 8.5 h at 0° C. 4 mL Water was added and the mixture was stirred for 1 h at room temperature followed by evaporation. Purification by reversed phase high performance liquid chromatography (RP HPLC) (semi-preparative column; 30-55% in 10 min) followed by lyophilization yielded the titled compound (40 mg, 23%) as a colorless solid.

step 1.4 Preparation of (1S,2S,3R,4R,5R)-2-amino-5-((phosphonooxy)methyl)-cyclohexane-1,3,4-triol To a solution of 40 mg of the compound of step 1.3 (0.068 mmol) in MeOH (2 mL) was added 10% Pd on carbon catalyst (10 mg) and the mixture was vigorously stirred under a hydrogen atmosphere (1 atm) at room temperature for 4 h. After filtration and lyophilization, the titled compound was obtained as a colorless solid (16 mg, 98%).

EXAMPLE 2

Determination of the in vitro Activation of the Self Cleavage of the glmS Riboswitch by the Compounds According to Formulas (1) and (3)

The determination was performed using an in vitro preparation of the glmS riboswitch of *Staphylococcus aureus* MU50.

Sample Preparation

The glmS riboswitch DNA was amplified from genomic DNA of the *S. aureus* Mu50 strain (RKI Berlin) by standard Pfu polymerase chain reaction (PCR) using a 5' primer containing the T7 promoter (GAT AAT ACG ACT CAC TAT AGG GCA GTT AAA GCG CCT GTG CAA ATA, SEQ ID NO: 1) and a 3' primer (ATC TTA TTA ACT TTG TCC ATT AAG TCA CCC, SEQ ID NO: 2) (20 cycles, annealing temperature of 60° C., homemade Pfu enzyme). The resultant of a 100 µl PCR reaction was phenol/chloroform extracted and precipitated using 3M NaOAc pH 5.4 and ethanol Pellets were resuspended in 10 µl diethylpyrocarbonate treated water (DEPC $H_2O$) and used as template for T7 RNA polymerase-based transcription. The transcription reaction contained the following components (concentrations stated as final concentrations): transcription buffer 40 mM Hepes KOH pH 7.9, 25 mM $MgCl_2$, 5 mM DTT, 2.5 mM of each NTP, 0.5 U/µl RNasin (Promega), 1.5-3 mM DNA template, 0.5 U/µl T7 RNA polymerase (homemade), DEPC $H_2O$ ad 100 µl. Incubation occurred at 37° C. over night and was followed by RNA work-up using PAGE (10% PAA-gel) and standard gel extraction and RNA precipitation procedures.

Hereafter, the *S. aureus* glmS riboswitch RNA was dephosphorylated on its 5' end using the calf intestine alkaline phosphatase (CIAP, Promega). Finally, 45 pmol of dephosphorylated RNA were used for phosphorylation using gamma $^{32}P$-ATP (10 mCi/ml NEN, Zaventem, Belgium) and the T4 polynucleotide kinase (NEB). After incubation at 37° C. for 30 min the reaction was passed through a G25 sepharose column (GE Healthcare) which had been equilibrated with DEPC $H_2O$ before, to exclude unincorporated radioactive nucleotides. Eventually the RNA was PAGE purified and precipitated. The pellets were dissolved in an appropriate volume of DEPC $H_2O$ and stored at −20° C. until use.

Metabolite-Induced Self-Cleavage Assay

For this assay the following components were mixed to yield the stated final concentrations: cleavage buffer (50 mM Hepes pH 7.5, 200 mM KCl), $MgCl_2$ (10 mM), glucosamine-6-phosphate (200 µM), glucosamine (GlcN) (200 µM), the compound according to formula (I) (200 µM) or the compound according to formula (3) (200 µM and 20 mM), radioactively labelled RNA (20 cps) and DEPC $H_2O$ ad 10 µl. Each reaction was prepared in a 1.5 µl Eppendorf tube. RNA was added last, after having been heated to 85° C. for 2 min and slowly cooled-down to room temperature for 10 min. The cleavage reaction was then incubated at 37° C. for 30 min and stopped by the addition of 5 µl sucrose PAGE loading buffer. Samples were loaded on thin 17% PAA gels and run at 400-600V for 2-4 hours. Irradiation of the phosphorimager screen was performed over night at −80° C. The screens were read using a FujiFilm PhosphorImager FLA 3000 and evaluated using AIDA software.

Figure 2:
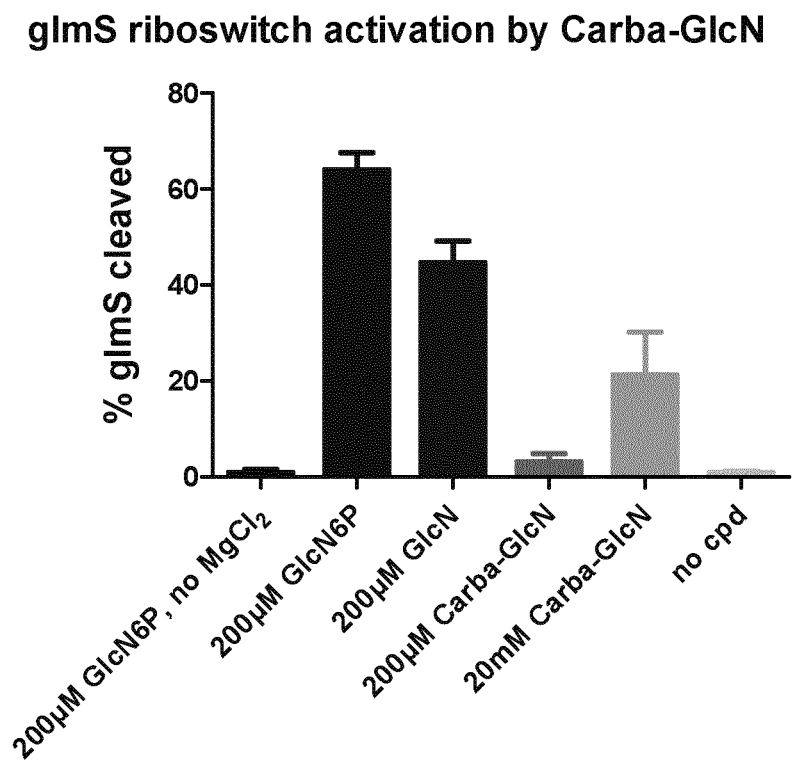
FIG. 2 in vitro activation of the self cleavage of the glmS riboswitch by glucosamine-6-phosphate (GlcN6P), glucosamine (GlcN) and by the compound according to formula (3), Carba-glucosamine (Carba-GlcN)

As can be seen in FIG. 1, the compound according to formula (I) (carba-GlcN6P) was shown to induce glmS-riboswitch self-cleavage very efficiently at a concentration of 200 µM. Concentration dependent analysis revealed an EC50-value of 6.24±0.66 µM compared to 3.61±0.39 µM found for glucosamine-6-phosphate (GlcN6P). As can be seen in FIG. 2, the compound according to formula (3) (carba-GlcN) also was able to induce glmS-riboswitch self-cleavage efficiently at a concentration of 200 µM and 20 mM.

EXAMPLE 3

Determination of the Minimal Concentration for the Inhibition in Staphylococcus aureus SG511

The determination of the minimal inhibitory concentration (MIC) of the compounds according to formula (I) (carba-GlcN6P) and formula (3) (carba-GlcN) was performed in clear, round bottom 96-well plates. For this 100 µl of 0.5× Mueller-Hinton media (Oxoid, 300 gm/litre dehydrated infusion from beef, 17.5 gm/litre casein hydrolysate, 1.5 gm/litre starch, pH 7.3) were put into the 12 wells. To the first well 100 µl of 320 mM solution of carba-GlcN were added, mixed by pipetting and 100 µl of this mixture were transferred into the next well etc., generating a sequence final dilutions from 160 mM to 0.08 mM. Finally, SG511 cells that had been grown to an optical density ($OD_{600}$) of 1 were diluted in 0.5× Mueller-Hinton media 1:10 000. From this dilution 100 µl were added to the already prepared plate leading to a final compound concentration of 80 mM-0.04 mM. After incubation for 10 min at RT and vivid shaking, the 96-well plate was transferred to a 37° C. incubator. After 18-24 h of incubation the plate was read at 600 nm using a standard plate reader.

Figure 3:
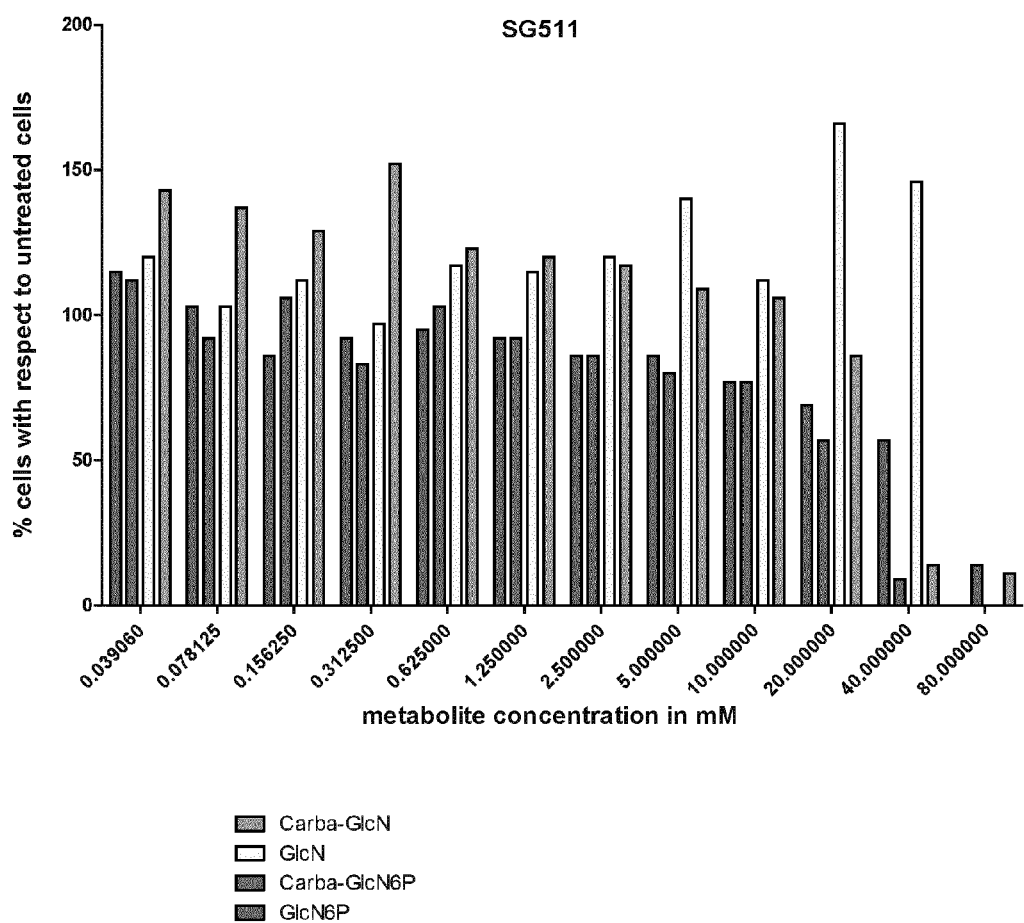
FIG. 3 Determination of the minimal concentration for the inhibition in Staphylococcus aureus SG511 for the compound according to formula (1), (Carba-GlcN6P), the compound according to formula (3) (Carba-GlcN), glucosamine-6-phosphate (GlcN6P), and glucosamine (GleN)

As can be seen in FIG. 3, bacterial growth was inhibited by the compounds according to the invention. These experiments show that the carba-analogues of GlcN6P according to formulas (1) and (3) can activate the glmS-riboswitch from S. aureus. Especially the compound according to formula (1) is able to activate the metabolite-dependent glmS-riboswitch from S. aureus with almost the same potency, as does the native metabolite.

These experiments further show that since the glmS-riboswitch is involved in the regulation of early steps of cell wall biosynthesis and interference with cell wall biosynthesis represents a valuable strategy to inhibit bacterial growth, the compound according to the invention can serve as important lead structure for developing novel antibiotics.

EXAMPLE 4

Determination of the Growth Inhibition in Vancomycin Intermediate Resistant Staphylococcus aureus Mu50 in Sugar Free Medium For the preparation of 2× chemically defined medium (2×CDM), a minimal medium for Staphylococcus aureus without glucose, for the preparation of 500 ml the following components were mixed in individual groups before being combined:
Group I
5 mg $FeSO_4 \times 7\ H_2O$, 1 mg $Fe(NO_3)_3 \times 9\ H_2O$, and 5 mg $MnSO_4$ were dissolved in 1 ml of deionized distilled water ($ddH_2O$).
Group IIA
100 mg L-tryptophan and 50 mg L-cysteine were dissolved in 1 ml 2N HCl at 55° C.
Group IIB
100 mg L-leucin, 100 mg DL-alanin, 100 mg L-isoleucin, 100 mg L-methionine, 200 mg L-threonine, 100 mg L-arginine, 100 mg L-histidine, 100 mg L-valine, 100 mg L-lysine, and 100 mg L-glutamine were dissolved in 10 ml $ddH_2O$.
Group IIC
100 mg L-aspartate, 100 mg L-phenylalanine, 100 mg L-serine, 100 mg L-proline, 100 mg L-hydroxyproline, 100 mg glycine, 100 mg L-glutamate, and 100 mg L-tyrosine were each dissolved in 1 ml 2.5N NaOH at 55° C.
Group III
1 mg p-aminobenzoic acid, 1 mg biotin, 2.4 mg folic acid, 4 mg nicotinamide, 10 mg α-nicotinamide adeninedinucleotide, 8 mg D-pantothenic acid, 4 mg pyridoxal HCl, 4 mg pyridoxamin-di-HCl, 8 mg riboflavine, 4 mg thiamine HCl, and 0.5 mg Cobalamine (vit. B12) were dissolved in 10 ml $ddH_2O$, then 2.5N NaOH were added drop-wise until the solution got clear.
Group IV
20 mg Adenine, 20 mg Guanine HCl, and 20 mg Uracil were dissolved in 3 ml 2N HCl at 90° C.
Group V
200 mg $K_2HPO_4$, 1000 mg $KH_2PO_4$, 700 mg $MgSO_4 \times 7H_2O$, 7 mg $CaCl_2 \times 2H_2O$, 4500 mg $NaOAc \times 3H_2O$, and 13 g HEPES (4-(2-hydroxyethyl)-1-piperazineethanesulfonic acid) were dissolved in 350 ml $ddH_2O$.

After preparation of the individual groups, the groups I-IV were added to group V. The volume was adjusted to 480 ml with $ddH_2O$. The pH was adjusted to 7 using HCl followed by adjusting the volume to the final 500 ml. Before storage at 4° C. the medium was sterile filtered.

The determination of the decrease in bacterial growth of Staphylococcus aureus Mu50 cells (RKI Berlin) depending on the concentration of the compound according to formula (3) (C GlcN) was performed in clear, sterile, round bottom 96-well plates with lid. Before treatment, the cells were grown in 2×CDM medium without glucose at 37° C. for 24 h under vigorous shaking.

For the determination of the growth inhibition 100 µl of 2×CDM were put into each of 12 wells. To the first well 100 µl of a 320 mM solution of the compound according to formula (3) (C GlcN) were added, mixed by pipetting and 100 µl of this mixture were transferred into the next well etc., generating a sequence dilutions from 160 mM to 0.08 mM. Finally, Mu50 cells that had been grown to an optical density ($OD_{600}$) of 0.8 to 1 were diluted in 2×CDM to an optical density ($OD_{600}$) of 0.2. From this dilution 100 µl were added to the already prepared plate leading to a final compound concentration of 80 mM, 40 mM, 20 mM, 10 mM, 5 mM, 2.5 mM, 0.312 mM, 0.156 mM, and 0.04 mM and a final $OD_{600}$ of 0.1 per well at the beginning of the measurement. The 96 well plate was incubated at 37° C. in a Tecan Sunrise plate reader, which tracks the optical density ($OD_{600}$) in 10 minute intervals and automatically shakes the plate for one minute every two minutes. Minimal inhibitory concentration was read after 18 h to 24 h of incubation. Control cells were treated without compounds and with 0.01 mM vancomycin.

Figure 4:
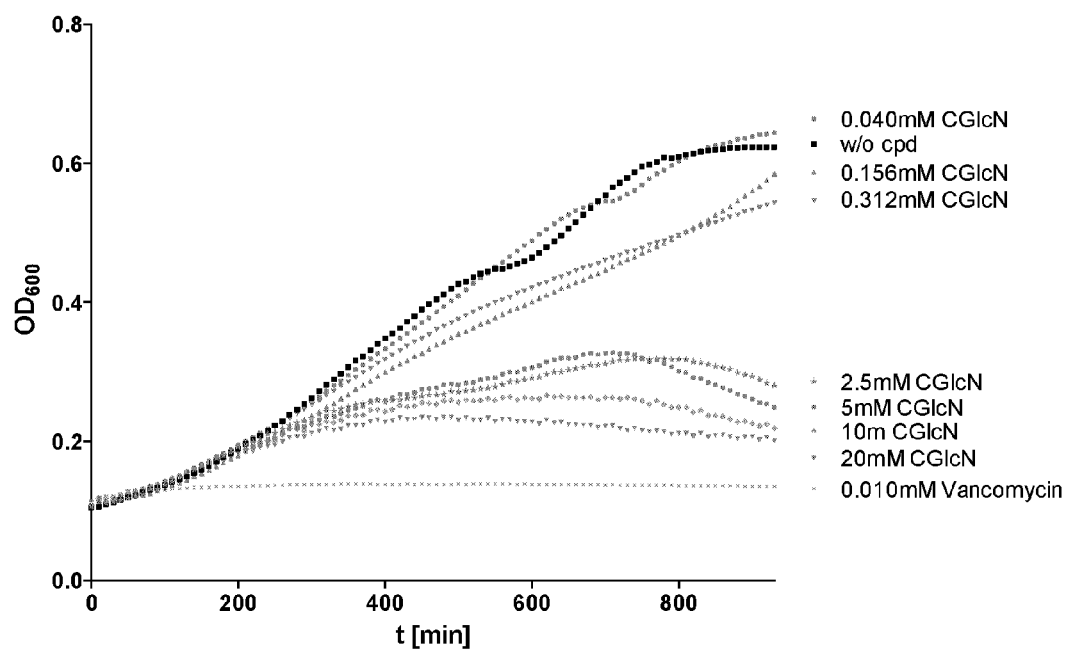
FIG. 4 the growth of Staphylococcus aureus Mu50 cells in the presence of 0.04 mM (dots), 0.156 mM (triangle, peaks up), 0.312 mM (hearts), 2.5 mM (stars), 5 mM (dots), 10 mM (checks), and 20 mM (triangle, peaks down) of the compound according to formula (3) (C GlcN), 0.01 mM vancomycin (black crosses), and without compounds (w/o cpd, black squares)

FIG. 4 shows the optical density ($OD_{600}$) of the bacterial growth of S. aureus Mu 50 cells in the presence of 0.04 mM (dots), 0.156 mM (triangle, peaks up), 0.312 mM (hearts), 2.5 mM (stars), 5 mM (dots), 10 mM (checks), and 20 mM (triangle, peaks down) of the compound according to formula (3) (C GlcN), the presence of 0.01 mM vancomycin (black crosses), and without compound (w/o cpd, black squares) over of 15 h of incubation. As can be seen in FIG. 4, a concentration dependent decrease in bacterial growth was observed for increased concentrations of the compound according to formula (3). A measureable growth inhibition in sugar free medium started at 0.156 mM of the compound according to formula (3) referring to the control cells grown without compounds. A more pronounced growth inhibition was observed at concentrations of 2.5 mM, 5 mM, 10 mM, and 20 mM of the compound according to formula (3). The minimal inhibitory concentration (MIC) values repeatedly (n=3) were observed at 0.625 mM of the compound according to formula (3).

EXAMPLE 5

Investigation of Synergistic Effects of the Compound According to Formula (3) in Vancomycin Treatment of S. aureus Mu50

The determination of the synergistic effects of the compound according to formula (3) in vancomycin treatment in *Staphylococcus aureus* Mu50 cells (RKI Berlin) was performed in clear, sterile, round bottom 96-well plates with lid. Before treatment, *Staphylococcus aureus* Mu50 cells (RKI Berlin) were grown in sterile, 15 ml flasks containing 5 ml of 2×CDM without glucose at 37° C. for 24 h under vigorous shaking.

For the determination of the growth inhibition 100 µl of 2×CDM containing 10 µM vancomycin were put into each of 12 wells. To the first well 100 µl of a 320 mM solution of the compound according to formula (3) (C GlcN) were added, mixed by pipetting and 100 µl of this mixture were transferred into the next well etc., generating a sequence dilutions from 160 mM to 5 mM. Finally, Mu50 cells that had been grown to an optical density ($OD_{600}$) of 0.8 to 1 were diluted in 2×CDM to an optical density ($OD_{600}$) of 0.2. From this dilution 100 µl were added to the already prepared plate leading to a final compound concentration of 80 mM, 40 mM, 20 mM, 10 mM, 5 mM, and 2.5 mM, a final concentration of 2.5 µM vancomycin and a final $OD_{600}$ of 0.1 per well at the beginning of the measurement. The 96 well plate was incubated at 37° C. in a Tecan Sunrise plate reader, which tracks the optical density ($OD_{600}$) in 10 minute intervals and automatically shakes the plate for one minute every two minutes. Minimal inhibitory concentration was read after 18 h to 24 h of incubation. Control cells were treated without compounds or with 2.5 µM vancomycin.

Figure 5:
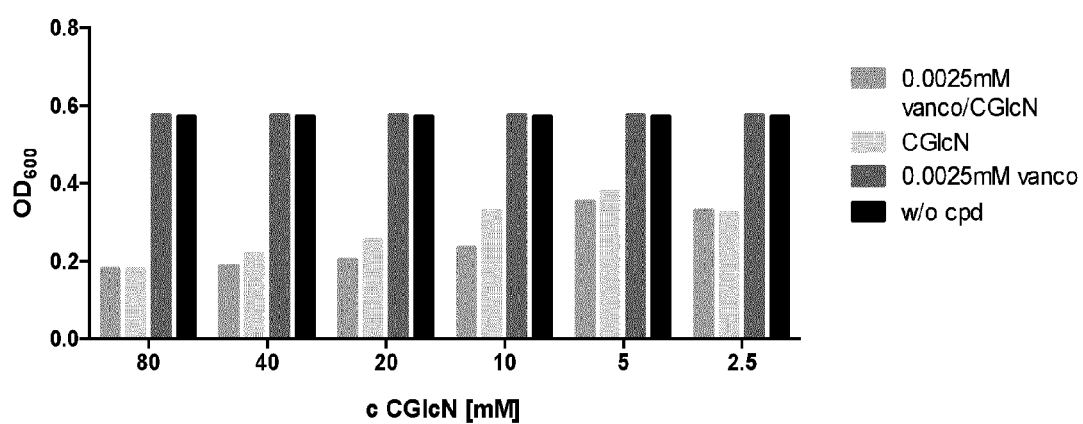
FIG. 5 a bar diagram showing the bacterial growth after 10 h in the presence of 2.5 mM, 5 mM, 10 mM, 20 mM, 40 mM, and 80 mM of the compound according to formula (3) (C GlcN, light grey bars), 0.0025 mM vancomycin (vanco, dark grey bars), a combination of the compound according to formula (3) and 0.0025 mM vancomycin (vanco/C GlcN, grey bars), and without compounds (w/o cpd, black bars)

FIG. 5 shows a bar diagram of the optical density ($OD_{600}$) of the bacterial growth after 10 h growth in the presence of concentrations of 2.5 mM, 5 mM, 10 mM, 20 mM, 40 mM, and 80 mM of the compound according to formula (3). As can be seen in FIG. 5, after 10 h of bacterial growth a subinhibitory concentration of vancomycin of 0.0025 mM alone (vanco, dark grey bars) showed no change in the bacterial growth as compared to untreated cells (w/o cpd, black bars). Cells grown in the presence of a subinhibitory concentration of 0.0025 mM vancomycin and concentrations of 2.5 mM, 5 mM, 10 mM, 20 mM, 40 mM, and 80 mM of the compound according to formula (3) (vanco/C GlcN, grey bars) revealed a more prominent growth inhibition than seen for the compound according to formula (3) (C GlcN, light grey bars) alone at the same concentration.

Figure 6:
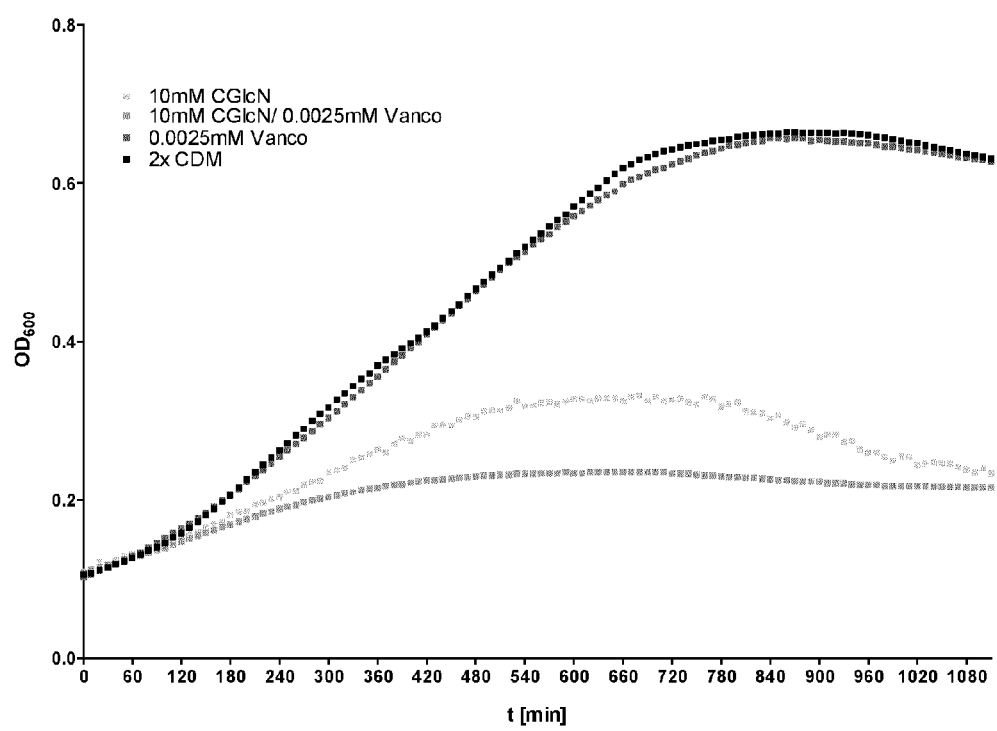
FIG. 6 the growth curves of S. aureus Mu 50 cells in the presence of 10 mM of the compound according to formula (3) (C GlcN, light grey squares), 0.0025 mM vancomycin (vanco, dark grey squares), a combination of 10mM of the compound according to formula (3) and 0.0025 mM vancomycin (grey squares), and no compound (2× CDM, black squares).

FIG. 6 shows the optical density ($OD_{600}$) of the bacterial growth of *S. aureus* Mu 50 cells in the presence of 10 mM of the compound according to formula (3) (C GlcN, light grey squares), 0.0025 mM vancomycin (vanco, dark grey squares), a combination of 10 mM of the compound according to formula (3) and 0.0025 mM vancomycin (grey squares), and no compound (2×CDM, black squares) over the time period of 18 h of incubation. As can be seen in FIG. 6, a subinhibitory concentration of 0.0025 mM vancomycin over the period of 18 h of incubation showed no change in the bacterial growth as compared to the untreated cells. The growth curves of aureus Mu 50 cells grown in the presence of 0.0025 mM vancomycin and 10 mM of the compound according to formula (3) revealed a more prominent growth inhibition compared to a treatment with 10 mM of the compound according to formula (3) alone.

These experiments show that a combination of the compound according to formula (3) and a subinhibitory concentration of vancomycin have a synergistic effect on the growth inhibition of bacterial cells.

---

---

The invention claimed is:

1. A compound according to general formula (I) as given as follows and/or racemates, enantiomers, diastereomers, solvates, hydrates, and pharmaceutically acceptable salts and/or esters thereof:

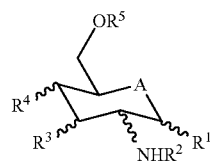

wherein:
R¹ is selected from the group comprising H, OH, SH and/or $NH_2$;
R² is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;
R³ is selected from the group comprising OH, SH and/or $NH_2$;
R⁴ is selected from the group comprising OH, SH and/or $NH_2$;
R⁵ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

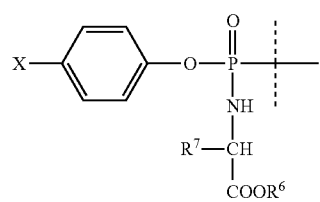

wherein:
R⁶ is selected from the group comprising linear or branched $C_1$-$C_6$-alkyl, benzyl and/or cyclohexyl;
R⁷ is a side chain of an amino acid selected from the group comprising hydrogen; linear or branched $C_1$-$C_4$-alkyl; linear or branched alkyl groups of the type —$C_nH_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$-$C_6H_4$-Y wherein Y is selected from the group comprising OH, SH, $C_1$-$C_3$-alkyl and/or $NH_2$; —$CH_2$-imidazole; —$CH_2$-indole; —$CH_2$-(furanyl-3-yl); —$CH_2$-(pyridyl-3-yl) and/or —$CH_2$-(imidazolyl-3-yl);
X is selected from the group comprising Cl, Br, I, $C_1$-$C_6$-alkyl and/or $C_1$-$C_6$-alkoxy;
A is selected from the group comprising S, NR⁸, $C=CR^8R^9$ and/or $CR^8R^9$, wherein
R⁸, R⁹ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker.

2. The compound according to claim 1, characterized in that A is a group —$CH_2$- and the compound has the formula (III) as indicated below and/or racemates, enantiomers, diastereomers, solvates, hydrates, and pharmaceutically acceptable salts and/or esters thereof:

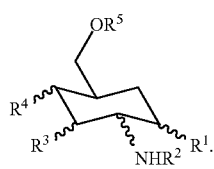

3. The compound according to claim 1 wherein R¹, R³ and R⁴ are OH.

4. The compound according to claim 1 wherein R² is selected from the group comprising hydrogen, $C_1$-$C_5$-alkyl preferably methyl, ethyl or n-propyl, benzyl, $C_1$-$C_5$-acyl preferably $C(O)CH_3$, $C(O)C_2H_5$, $C(O)$n-propyl or $C(O)$iso-propyl, $C(O)NH_2$, $NH_2$ and/or $S(O)_2OH$.

5. The compound according to claim 1, wherein R⁵ is selected from the group comprising hydrogen, $P(O)(OH)_2$ and/or aryloxy phosphoramidates according to general formula (II) wherein R⁶ is methyl, ethyl, isopropyl, cyclohexyl or benzyl, X is methoxy and R⁷ is methyl, preferably R⁵ is $P(O)(OH)_2$.

6. The compound according to claim 1, wherein the compound is selected from the group comprising the formulas (1) and/or (2) as indicated below and/or racemates, enantiomers, diastereomers, solvates, hydrates, and pharmaceutically acceptable salts and/or esters thereof:

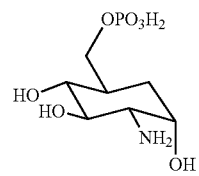

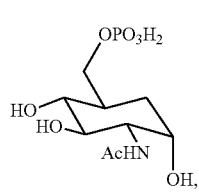

wherein
Ac is acetyl.

7. The compound according to claim 1, wherein the compound according to general formula (I) is part of a dimer, trimer or oligomer, formed from one compound according to any one of the foregoing claims and at least one other compound joined together via a linker linked to element A, preferably a linker selected from the group comprising nucleotide linkers, polyethylene glycols, peptide linkers and/or linear or branched, saturated or unsaturated $C_1$-$C_{50}$-alkyl.

8. The compound according to general formula (I) as given as follows and/or racemates, enantiomers, diastereomers, solvates, hydrates, and pharmaceutically acceptable salts and/or esters thereof:

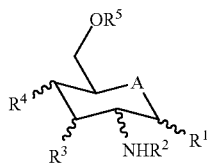

(I)

wherein:
R$^1$ is selected from the group comprising H, OH, SH and/or NH$_2$;
R$^2$ is selected from the group comprising hydrogen, C$_1$-C$_{10}$-alkyl, C$_7$-C$_{14}$-arylalkyl wherein the aryl group has 6 to 10 carbon atoms and the alkyl group has 1 to 4 carbon atoms, C(O)C$_1$-C$_{10}$-alkyl, OC(O)C$_1$-C$_{10}$-alkyl, C(O)OC$_1$-C$_{10}$-alkyl, C(O)NH$_2$, NH$_2$ and/or S(O)$_2$OH;
R$^3$ is selected from the group comprising OH, SH and/or NH$_2$;
R$^4$ is selected from the group comprising OH, SH and/or NH$_2$;
R$^5$ is selected from the group comprising hydrogen, P(O)(OH)$_2$, S(O)$_2$OH, P(S)(OH)$_2$, P(O)OHSH, S(O)$_2$SH and/or aryloxy phosphoramidates according to general formula (II)

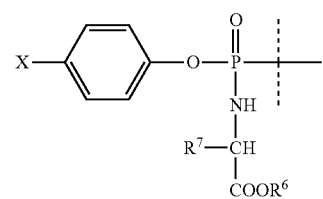

(II)

wherein:
R$^6$ is selected from the group comprising linear or branched C$_1$-C$_6$-alkyl, benzyl and/or cyclohexyl;
R$^7$ is a side chain of an amino acid selected from the group comprising hydrogen; linear or branched C$_1$-C$_4$-alkyl; linear or branched alkyl groups of the type -C$_１$H$_{2n}$-U-D wherein n is 1, 2, 3 or 4, U is selected from the group comprising O, CO, COO, CONH, S, guanidine and/or NH and D is selected from the group comprising H and/or C$_1$-C$_3$-alkyl; —CH$_2$-C$_6$H$_4$-Y wherein Y is selected from the group comprising OH, SH, C$_1$-C$_3$-alkyl and/or NH$_2$; —CH$_2$-imidazole; —CH$_2$-indole; —CH$_2$-(furanyl-3-yl); —CH$_2$-(pyridyl-3-yl) and/or —CH$_2$-(imidazolyl-3-yl);
X is selected from the group comprising Cl, Br, I, C$_1$-C$_6$-alkyl and/or C$_1$-C$_6$-alkoxy;
A is selected from the group comprising S, NR$^8$, C=CR$^8$R$^9$ and/or CR$^8$R$^9$, wherein
R$^8$, R$^9$ is selected, the same or each independently of the other, from the group comprising hydrogen, C$_1$-C$_{10}$-alkyl, C$_2$-C$_{10}$-alkenyl, C$_6$-C$_{10}$-aryl, C$_7$-C$_{14}$-arylalkyl wherein the aryl group has 6 to 10 carbon atoms and the alkyl group has 1 to 4 carbon atoms, C(O)C$_1$-C$_{10}$-alkyl, C(O)OC$_1$-C$_{10}$-alkyl, C(O)NH$_2$, NH$_2$, S(O)$_2$OH and/or a linker,
for use as a medicament.

9. The compound according to general formula (I) as given as follows and/or racemates, enantiomers, diastereomers, solvates, hydrates, and pharmaceutically acceptable salts and/or esters thereof:

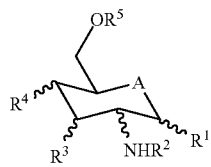

(I)

wherein:
R$^1$ is selected from the group comprising H, OH, SH and/or NH$_2$;
R$^2$ is selected from the group comprising hydrogen, C$_1$-C$_{10}$-alkyl, C$_7$-C$_{14}$-arylalkyl wherein the aryl group has 6 to 10 carbon atoms and the alkyl group has 1 to 4 carbon atoms, C(O)C$_1$-C$_{10}$-alkyl, OC(O)C$_1$-C$_{10}$-alkyl, C(O)OC$_1$-C$_{10}$-alkyl, C(O)NH$_2$, NH$_2$ and/or S(O)$_2$OH;
R$^3$ is selected from the group comprising OH, SH and/or NH$_2$;
R$^4$ is selected from the group comprising OH, SH and/or NH$_2$;
R$^5$ is selected from the group comprising hydrogen, P(O)(OH)$_2$, S(O)$_2$OH, P(S)(OH)$_2$, P(O)OHSH, S(O)$_2$SH and/or aryloxy phosphoramidates according to general formula (II)

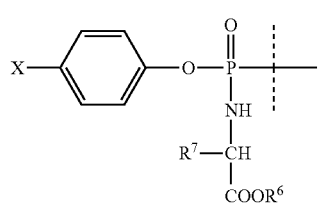

(II)

wherein:
R$^6$ is selected from the group comprising linear or branched C$_1$-C$_6$-alkyl, benzyl and/or cyclohexyl;
R$^7$ is a side chain of an amino acid selected from the group comprising hydrogen; linear or branched C$_1$-C$_4$-alkyl; linear or branched alkyl groups of the type -C$_n$H$_{2n}$-U-D wherein n is 1, 2, 3 or 4, U is selected from the group comprising O, CO, COO, CONH, S, guanidine and/or NH and D is selected from the group comprising H and/or C$_1$-C$_3$-alkyl; —CH$_2$-C$_6$H$_4$-Y wherein Y is selected from the group comprising OH, SH, C$_1$-C$_3$-alkyl and/or NH$_2$; —CH$_2$-imidazole; —CH$_2$-indole; —CH$_2$-(furanyl-3-yl); —CH$_2$-(pyridyl-3-yl) and/or —CH$_2$-(imidazolyl-3-yl);
X is selected from the group comprising Cl, Br, I, C$_1$-C$_6$-alkyl and/or C$_1$-C$_6$-alkoxy;
A is selected from the group comprising S, NR$^8$, C=CR$^8$R$^9$ and/or CR$^8$R$^9$, wherein
R$^8$, R$^9$ is selected, the same or each independently of the other, from the group comprising hydrogen, C$_1$-C$_{10}$-alkyl, C$_2$-C$_{10}$-alkenyl, C$_6$-C$_{10}$-aryl, C$_7$-C$_{14}$-arylalkyl wherein the aryl group has 6 to 10 carbon atoms and the alkyl group has 1 to 4 carbon atoms, C(O)C$_1$-C$_{10}$-alkyl, C(O)OC$_1$-C$_{10}$-alkyl, C(O)NH$_2$, NH$_2$, S(O)$_2$OH and/or a linker,
for use in the therapeutic and/or prophylactic treatment of a bacterial infection, particularly for use as an antibiotic.

10. A pharmaceutical composition comprising as an active ingredient a compound according to general formula (I) as given as follows and/or racemates, enantiomers, diastereomers, solvates, hydrates, and pharmaceutically acceptable salts and/or esters thereof:

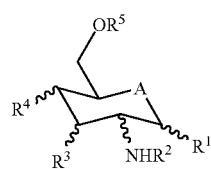
(I)

wherein:
- $R^1$ is selected from the group comprising H, OH, SH and/or $NH_2$;
- $R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;
- $R^3$ is selected from the group comprising OH, SH and/or $NH_2$;
- $R^4$ is selected from the group comprising OH, SH and/or $NH_2$;
- $R^5$ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

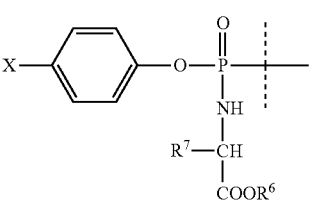
(II)

wherein:
- $R^6$ is selected from the group comprising linear or branched $C_1$-$C_6$-alkyl, benzyl and/or cyclohexyl;
- $R^7$ is a side chain of an amino acid selected from the group comprising hydrogen; linear or branched $C_1$-$C_4$-alkyl; linear or branched alkyl groups of the type -$C_1H_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$-$C_6H_4$-Y wherein Y is selected from the group comprising OH, SH, $C_1$-$C_3$-alkyl and/or $NH_2$; -$CH_2$-imidazole; —$CH_2$-indole; —$CH_2$-(furanyl-3-yl); -$CH_2$-(pyridyl-3-yl) and/or -$CH_2$-(imidazolyl-3-yl);
- X is selected from the group comprising Cl, Br, I, $C_1$-$C_6$-alkyl and/or $C_1$-$C_6$-alkoxy;
- A is selected from the group comprising S, $NR^8$, $C=CR^8R^9$ and/or $CR^8R^9$, wherein
  - $R^8$, $R^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker 11. A pharmaceutical composition comprising as an active ingredient a combination of a compound according to general formula (I) and/or racemates, enantiomers, diastereomers, solvates, hydrates, and pharmaceutically acceptable salts and/or esters thereof:

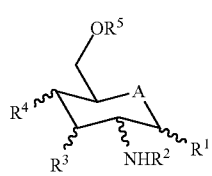
(I)

wherein:
- $R^1$ is selected from the group comprising H, OH, SH and/or $NH_2$;
- $R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;
- $R^3$ is selected from the group comprising OH, SH and/or $NH_2$;
- $R^4$ is selected from the group comprising OH, SH and/or $NH_2$;
- $R^5$ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

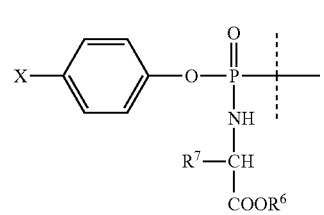
(II)

wherein:
- $R^6$ is selected from the group comprising linear or branched $C_1$-$C_6$-alkyl, benzyl and/or cyclohexyl;
- $R^7$ is a side chain of an amino acid selected from the group comprising hydrogen;
- linear or branched $C_1$-$C_4$-alkyl; linear or branched alkyl groups of the type -$C_1H_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$-$C_6H_4$-Y wherein Y is selected from the group comprising OH, SH, $C_1$-$C_3$-alkyl and/or $NH_2$; —$CH_2$-imidazole; —$CH_2$-indole; —$CH_2$-(furanyl-3-yl); —$CH_2$-(pyridyl-3-yl) and/or —$CH_2$-(imidazolyl-3-yl);
- X is selected from the group comprising Cl, Br, I, $C_1$-$C_6$-alkyl and/or $C_1$-$C_6$-alkoxy;
- A is selected from the group comprising S, $NR^8$, $C=CR^8R^9$ and/or $CR^8R^9$, wherein
  - $R^8$, $R^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker, and vancomycin.

12. Antibiotic comprising as an active ingredient a compound according to general formula (I) as given as follows and/or racemates, enantiomers, diastereomers, solvates, hydrates, and pharmaceutically acceptable salts and/or esters thereof:

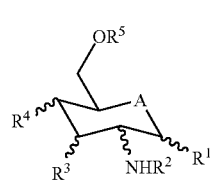 (I)

wherein:
R$^1$ is selected from the group comprising H, OH, SH and/or NH$_2$;
R$^2$ is selected from the group comprising hydrogen, C$_1$-C$_{10}$-alkyl, C$_7$-C$_{14}$-arylalkyl wherein the aryl group has 6 to 10 carbon atoms and the alkyl group has 1 to 4 carbon atoms, C(O)C$_1$-C$_{10}$-alkyl, OC(O)C$_1$-C$_{10}$-alkyl, C(O)OC$_1$-C$_{10}$-alkyl, C(O)NH$_2$, NH$_2$ and/or S(O)$_2$OH;
R$^3$ is selected from the group comprising OH, SH and/or NH$_2$;
R$^4$ is selected from the group comprising OH, SH and/or NH$_2$;
R$^5$ is selected from the group comprising hydrogen, P(O)(OH)$_2$, S(O)$_2$OH, P(S)(OH)$_2$, P(O)OHSH, S(O)$_2$SH and/or aryloxy phosphoramidates according to general formula (II)

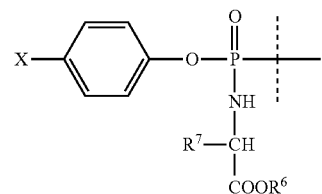 (II)

wherein:
R$^6$ is selected from the group comprising linear or branched C$_1$-C$_6$-alkyl, benzyl and/or cyclohexyl;
R$^7$ is a side chain of an amino acid selected from the group comprising hydrogen; linear or branched C$_1$-C$_4$-alkyl; linear or branched alkyl groups of the type —C$_n$H$_{2n}$-U-D wherein n is 1, 2, 3 or 4, U is selected from the group comprising O, CO, COO, CONH, S, guanidine and/or NH and D is selected from the group comprising H and/or C$_1$-C$_3$-alkyl; —CH$_2$-C$_6$H$_4$-Y wherein Y is selected from the group comprising OH, SH, C$_1$-C$_3$-alkyl and/or NH$_2$; —CH$_2$-imidazole; —CH$_2$-indole; —CH$_2$-(furanyl-3-yl); -CH$_2$-(pyridyl-3-yl) and/or -CH$_2$-(imidazolyl-3-yl);
X is selected from the group comprising Cl, Br, I, C$_1$-C$_6$-alkyl and/or C$_1$-C$_6$-alkoxy;
A is selected from the group comprising S, NR$^8$, C=CR$^8$R$^9$ and/or CR$^8$R$^9$, wherein
R$^8$, R$^9$ is selected, the same or each independently of the other, from the group comprising hydrogen, C$_1$-C$_{10}$-alkyl, C$_2$-C$_{10}$-alkenyl, C$_6$-C$_{10}$-aryl, C$_7$-C$_{14}$-arylalkyl wherein the aryl group has 6 to 10 carbon atoms and the alkyl group has 1 to 4 carbon atoms, C(O)C$_1$-C$_{10}$-alkyl, C(O)OC$_1$-C$_{10}$-alkyl, C(O)NH$_2$, NH$_2$, S(O)$_2$OH and/or a linker.

13. A method for manufacturing a medicament comprising the steps of preparing a compound, suitable for administration, having a general formula (I) as given as follows and/or racemates, enantiomers, diastereomers, solvates, hydrates, and pharmaceutically acceptable salts and/or esters thereof:

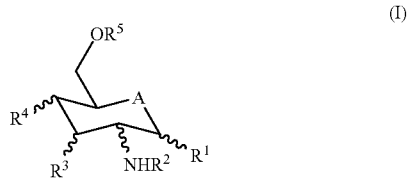 (I)

wherein:
R$^1$ is selected from the group comprising H, OH, SH and/or NH$_2$;
R$^2$ is selected from the group comprising hydrogen, C$_1$-C$_{10}$-alkyl, C$_7$-C$_{14}$-arylalkyl wherein the aryl group has 6 to 10 carbon atoms and the alkyl group has 1 to 4 carbon atoms, C(O)C$_1$-C$_{10}$-alkyl, OC(O)C$_1$-C$_{10}$-alkyl, C(O)OC$_1$-C$_{10}$-alkyl, C(O)NH$_2$, NH$_2$ and/or S(O)$_2$OH;
R$^3$ is selected from the group comprising OH, SH and/or NH$_2$;
R$^4$ is selected from the group comprising OH, SH and/or NH$_2$;
R$^5$ is selected from the group comprising hydrogen, P(O)(OH)$_2$, S(O)$_2$OH, P(S)(OH)$_2$, P(O)OHSH, S(O)$_2$SH and/or aryloxy phosphoramidates according to general formula (II)

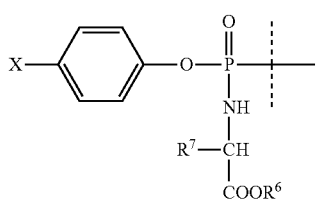 (II)

wherein:
R$^6$ is selected from the group comprising linear or branched C$_1$-C$_6$-alkyl, benzyl and/or cyclohexyl;
R$^7$ is a side chain of an amino acid selected from the group comprising hydrogen; linear or branched C$_1$-C$_4$-alkyl; linear or branched alkyl groups of the type —C$_1$H$_{2n}$-U-D wherein n is 1, 2, 3 or 4, U is selected from the group comprising O, CO, COO, CONH, S, guanidine and/or NH and D is selected from the group comprising H and/or C$_1$-C$_3$-alkyl; —CH$_2$-C$_6$H$_4$-Y wherein Y is selected from the group comprising OH, SH, C$_1$-C$_3$-alkyl and/or NH$_2$; —CH$_2$-imidazole; —CH$_2$-indole; —CH$_2$-(furanyl-3-yl); —CH$_2$-(pyridyl-3-yl) and/or —CH$_2$-(imidazolyl-3-yl);
X is selected from the group comprising Cl, Br, I, C$_1$-C$_6$-alkyl and/or C$_1$-C$_6$-alkoxy;
A is selected from the group comprising S, NR$^8$, C=CR$^8$R$^9$ and/or CR$^8$R$^9$, wherein
R$^8$, R$^9$ is selected, the same or each independently of the other, from the group comprising hydrogen, C$_1$-C$_{10}$- alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $C(O)OC_1$-$C_{10}$-alkyl, $C(O)NH_2$, $NH_2$, $S(O)_2OH$ and/or a linker.

14. A method for treating a bacterial infection comprising the steps of administering to a subject a compound according to general formula (I) as given as follows and/or racemates, enantiomers, diastereomers, solvates, hydrates, and pharmaceutically acceptable salts and/or esters thereof:

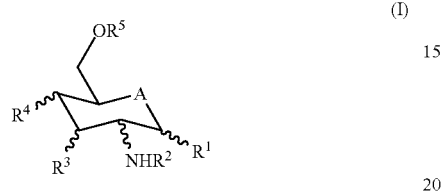
(I)

wherein:
$R^1$ is selected from the group comprising H, OH, SH and/or $NH_2$;
$R^2$ is selected from the group comprising hydrogen, $C_1$-$C_{10}$-alkyl, $C_7$-$C_{14}$-arylalkyl wherein the aryl group has 6 to 10 carbon atoms and the alkyl group has 1 to 4 carbon atoms, $C(O)C_1$-$C_{10}$-alkyl, $OC(O)C_1$-$C_{10}$-alkyl, $C(O)OC_1$-$C_{10}$-alkyl, $C(O)NH_2$, $NH_2$ and/or $S(O)_2OH$;
$R^3$ is selected from the group comprising OH, SH and/or $NH_2$;
$R^4$ is selected from the group comprising OH, SH and/or $NH_2$;
$R^5$ is selected from the group comprising hydrogen, $P(O)(OH)_2$, $S(O)_2OH$, $P(S)(OH)_2$, $P(O)OHSH$, $S(O)_2SH$ and/or aryloxy phosphoramidates according to general formula (II)

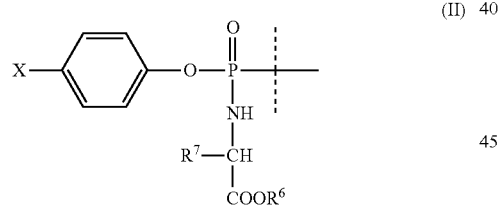
(II)

wherein:
$R^6$ is selected from the group comprising linear or branched $C_1$-$C_6$-alkyl, benzyl and/or cyclohexyl;

$R^7$ is a side chain of an amino acid selected from the group comprising hydrogen; linear or branched $C_1$-$C_4$-alkyl; linear or branched alkyl groups of the type —$C_nH1_{2n}$-U-D wherein n is 1, 2, 3 or 4, U is selected from the group comprising O, CO, COO, CONH, S, guanidine and/or NH and D is selected from the group comprising H and/or $C_1$-$C_3$-alkyl; —$CH_2$-$C_6H_4$-Y wherein Y is selected from the group comprising OH, SH, $C_1$-$C_3$-alkyl and/or $NH_2$; —$CH_2$-imidazole; —$CH_2$-indole; —$CH_2$-(furanyl-3-yl); —$CH_2$-(pyridyl-3-yl) and/or —$CH_2$-(imidazolyl-3-yl);
X is selected from the group comprising Cl, Br, I, $C_1$-$C_6$-alkyl and/or $C_1$-$C_6$-alkoxy;
A is selected from the group comprising S, $NR^8$, $C=CR^8R^9$ and/or $CR^8R^9$, wherein
$R^8$, $R^9$ is selected, the same or each independently of the other, from the group comprising hydrogen, $C_1$-$C_{10}$-alkyl, $C_2$-$C_{10}$-alkenyl, $C_6$-$C_{10}$-aryl, $C_7$-$C_{14}$-arylalkyl wherein the aryl group has 6 to 10 carbon atoms and the alkyl group has 1 to 4carbon atoms, $C(O)C_1$-$C_{10}$-alkyl, $C(O)OC_1$-$C_{10}$-alkyl, $C(O)NH_2$, $NH_2$, $S(O)_2OH$ and/or a linker.

15. A method for preparing a compound according to claim 1, wherein $R^5$ is $P(O)(OH)_2$ comprising the steps of:
a) Providing a cyclohexane according to formula (IV)

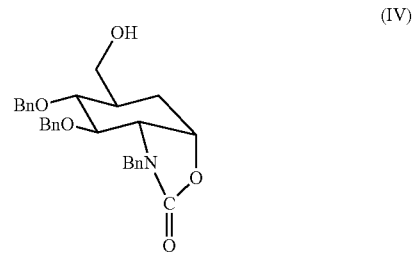 [SMILES: O=C1OC2CC(CO)C(OCc3ccccc3)C(OCc3ccccc3)C2N1Cc1ccccc1]
(IV)

b) Alkaline hydrolysis of the carbamate moiety to a 1-hydroxy-2-benzylamino moiety;
c) Selective introduction of a phosphate group to the primary hydroxyl group of the hydrolysed cyclohexane of step b);
d) Reduction of the benzyl protecting groups to the respective alcohol and amine groups of the cyclohexane of step c).

16. The method of claim 14, wherein the bacterial infection is multiresistant Staphylcoccus aureus (MRSA).

17. The method of claim 14, further comprising the step of inhibiting bacterial growth of the bacterial infection.

* * * * *

UNITED STATES PATENT AND TRADEMARK OFFICE
CERTIFICATE OF CORRECTION

PATENT NO. : 8,846,645 B2  
APPLICATION NO. : 13/990801  
DATED : September 30, 2014  
INVENTOR(S) : Günter Mayer et al.

Page 1 of 1

It is certified that error appears in the above-identified patent and that said Letters Patent is hereby corrected as shown below:

In the Specification

In column 5, Line 8, delete "R1, and R4" and insert --R1, R3 and R4--.

In column 7, Line 36, after the word "group" insert a --.--.

In column 11, Line 5, after the word "group" insert a --.--.

In column 12, Line 3, delete "NRB" and insert --NR8--.

In column 12, Line 55, delete "R1, and R4" and insert --R1, R3 and R4--.

In column 14, Line 28, after the word "group" insert a --.--.

In column 17, Line 32, after the word "group" insert a --.--.

In column 20, Line 54, after the word "group" insert a --.--.

In column 25, Line 53, after the word "group" insert a --.--.

In the Claims

In column 35, Line 43 (claim 8), delete "C1H2n-U-D" and insert --CnH2n-U-D--.

In column 37, Line 49 (claim 10), delete "C1H2n-U-D" and insert --CnH2n-U-D--.

In column 39, Line 51 (claim 12), delete "C1H2n-U-D" and insert --CnH2n-U-D--.

Signed and Sealed this  
Seventh Day of July, 2015

Michelle K. Lee  
*Director of the United States Patent and Trademark Office*